United States Patent
Alam et al.

(10) Patent No.: US 7,425,443 B2
(45) Date of Patent: *Sep. 16, 2008

(54) TREATMENT OF DIABETES WITH SYNTHETIC BETA CELLS

(75) Inventors: Tausif Alam, Madison, WI (US); Debra A. Hullett, Madison, WI (US); Hans W. Sollinger, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 218 days.

This patent is subject to a terminal disclaimer.

(21) Appl. No.: 11/127,629

(22) Filed: May 12, 2005

(65) Prior Publication Data

US 2005/0265972 A1    Dec. 1, 2005

Related U.S. Application Data

(63) Continuation-in-part of application No. 10/923,924, filed on Aug. 23, 2004, now abandoned, which is a continuation of application No. 10/013,032, filed on Nov. 12, 2001, now Pat. No. 6,933,133, which is a continuation of application No. 09/537,696, filed on Mar. 28, 2000, now Pat. No. 6,352,857, which is a continuation-in-part of application No. 09/115,888, filed on Jul. 15, 1998, now abandoned, which is a continuation-in-part of application No. 08/786,625, filed on Jan. 21, 1997, now abandoned.

(51) Int. Cl.
C12N 15/00 (2006.01)
A01N 63/00 (2006.01)

(52) U.S. Cl. .............. 435/320.1; 424/93.2; 424/93.21; 536/23.5; 536/24.1

(58) Field of Classification Search ................. None
See application file for complete search history.

(56) References Cited

OTHER PUBLICATIONS

Robbins et al, Pharmacol Ther 1998;80:35-47.*
Jeffe et al, Nat Genet 1992;1:372-8.*
Verma et al, Nature 1997;389;239-42.*
Freeman et al, Intl J Mol Med 1999; 4:585-592.*
Miller et al, 1995, FASEB J., vol. 9, pp. 190-199.*
Orkin et al. NIH Report, Dec. 1995.*
Peterson, Statement of Amy Patterson M.D., Feb. 2000.*
Levine et al, Mol Med Today Apr. 1999;5:165-171.*
Ludwig et al, Curr Opin Organ Transplant 2006;11:94-100.*
Han B & Zhang J, "Regulation of gene expression by internal ribosome entry sites or cryptic promoters: the eIF4G story," Mol. Cell. Biol. 22:7372-7384 (2002).
Han B, et al., "Tight control of platelet-derived growth factor B/c-sis expression by interplay between the 5'-untranslated region sequence and the major upstream promoter," J. Biol. Chem. 278:46983-46993 (2003).
Pedersen S, et al., "Human insulin-like growth factor II leader 2 mediates internal initiation of translation," Biochem. J. 363:37-44 (2002).
Yang Q & Sarnow P, "Location of the internal ribosome entry site in the 5' non-coding region of the immunoglobulin heavy-chain binding protein (BiP) mRNA: evidence for specific RNA-protein interactions," Nucleic Acids Res. 25:2800-2807 (1997).

* cited by examiner

*Primary Examiner*—Q. Janice Li
(74) *Attorney, Agent, or Firm*—Quarles & Brady LLP

(57) ABSTRACT

Disclosed is a method for obtaining glucose-regulated expression of active insulin in the cells of a mammalian subject. The method involves delivering into the subject a genetic construct comprising a coding sequence for a human proinsulin operably connected a promoter functional in the host cells. The construct includes a glucose responsive regulatory module having at least one glucose inducible regulatory element comprising a pair of CACGTG motifs linked by a five base nucleotide sequence, which confers glucose inducible expression of the proinsulin coding sequence. To ensure proper processing of the proinsulin to active insulin, the coding sequence was modified to direct the synthesis of a mutant proinsulin polypeptide having amino acid sequences that can be cleaved to mature insulin in suitable host cells, such as hepatocytes.

13 Claims, 17 Drawing Sheets

- —○— TREATED (A=6)
- —◇— DIABETIC (A=5)
- --△-- NORMAL (A=3)

△ SZ-TREATED DIABETIC CONTROL RATS
◇○ Ad.hins TREATED DIABETIC RATS

3SATEM2B(KpnI)
SEQ ID NO:25

```
         NotI
GCGGCCGCCA GTTCT|CACGT G|GTGGC|CACG TG|CTTGGGCA CGCCAGTTCT      50

EcoR I
|CACGTG|GTGG C|CACGTG|CTT GGGCACGAAT TCCAGTTCT|C ACGTG|GTGGC    100

Xba I
|CACGTG|CTTG GGCACTCTAG AGGGATTTAG TTAAACAACT TTTTTTTTTC       150

TTTTTGGCAA GGATGGTATG ATTTTGTAAT GGGGTAGGAA CCAATGAAAT         200

GAAAGGTTAG TGTGGTTAAT GATCTACAGT TATTGGTTAG AGAAGTATAT         250

TAGAGCGAGT TTCTCTGCAC ACAGACCACC TTTCCTGTCA ACCCACTGCC         300

Kpn I
TCTGGTACCa gcgcagaggc ttggggcagc cgagcggcag ccaggccccg         350
gcccgggcct cggttccaga agggagagga gcccgccaag gcgcgcaaga         400
gagcgggctg cctcgcagtc cgagccggag agggagcgcg agccgcgccg         450

M
gccccggacg gcctccgaaa cc|ATG|GCCCT GTGGATGCGC CTCCTGCCCC       500

TGCTGGCGCT GCTGGCCCTC TGGGGACCTG ACCCAGCCGC AGCCTTTGTG         550

AACCAACACC TGTGCGGCTC ACACCTGGTG GAAGCTCTCT ACCTAGTGTG         600

K → R    R → K
CGGGGAACGA GGCTTCTTCT ACACACCCAg GACCaagCGG GAGGCAGAGG         650

ACCTGCAGGT GGGGCAGGTG GAGCTGGGCG GGGCCCTGG TGCAGGCAGC          700

CTGCAGCCCT TGGCCCTGGA GGGGTCCCGG CAGAAGCGTG GCATTGTGGA         750

ACAATGCTGT ACCAGCATCT GCTCCCTCTA CCAGCTGGAG AACTACTGCA         800

End             Sal I
AC|TAG|ACGCA GCCTGCAGGC AGCGTCGAC
```

Fig. 11b

```
                       SEQUENCE LISTING

<160> NUMBER OF SEQ ID NOS: 31

<210> SEQ ID NO 1
<211> LENGTH: 29
<212> TYPE: DNA
<213> ORGANISM: Artificial
<220> FEATURE:
<223> OTHER INFORMATION: oligonucleotide corresponding to human insulin

<400> SEQUENCE: 1
ggggtaccat cagaagaggc catcaagca                                           29

<210> SEQ ID NO 2
<211> LENGTH: 34
<212> TYPE: DNA
<213> ORGANISM: Artificial
<220> FEATURE:
<223> OTHER INFORMATION: oligonucleotide corresponding to human insulin

<400> SEQUENCE: 2
cggagtcgac catctctctc ggtgcaggag gcgg                                     34

<210> SEQ ID NO 3
<211> LENGTH: 25
<212> TYPE: DNA
<213> ORGANISM: Artificial
<220> FEATURE:
<223> OTHER INFORMATION: oligonucleotide corresponding to human insulin
      containing lysine and 2 arginine mutation

<400> SEQUENCE: 3
gaggggtccc ggcagaagcg tggca                                               25

<210> SEQ ID NO 4
<211> LENGTH: 25
<212> TYPE: DNA
<213> ORGANISM: Artificial
<220> FEATURE:
<223> OTHER INFORMATION: oligonucleotide corresponding to human insulin
      containing mutation

<400> SEQUENCE: 4
acgcttctgc cgggacccct ccagg                                               25

<210> SEQ ID NO 5
```

```
<211> LENGTH: 66
<212> TYPE: DNA
<213> ORGANISM: Artificial
<220> FEATURE:
<223> OTHER INFORMATION: glucose inducible regulatory element

<400> SEQUENCE: 5
ggccgctgtc acgtgggcgc cacgtgggcg ccacgtgggc gccacgtggg cgccacgtgg    60
gcgccg                                                              66

<210> SEQ ID NO 6
<211> LENGTH: 33
<212> TYPE: DNA
<213> ORGANISM: Artificial
<220> FEATURE:
<223> OTHER INFORMATION: oligonucleotide corresponding to rat albumin
      promoter

<400> SEQUENCE: 6
ggaattctct agagggattt agttaaacaa ctt                                 33

<210> SEQ ID NO 7
<211> LENGTH: 29
<212> TYPE: DNA
<213> ORGANISM: Artificial
<220> FEATURE:
<223> OTHER INFORMATION: oligonucleotide corresponding to rat albumin
      promoter

<400> SEQUENCE: 7
ggggtaccag aggcagtggg ttgacaggt                                      29

<210> SEQ ID NO 8
<211> LENGTH: 17
<212> TYPE: DNA
<213> ORGANISM: Artificial
<220> FEATURE:
<223> OTHER INFORMATION: 1 glucose inducible regulatory element

<400> SEQUENCE: 8
cacgtggtgg ccacgtg                                                   17

<210> SEQ ID NO 9
<211> LENGTH: 52
<212> TYPE: DNA
<213> ORGANISM: Artificial
<220> FEATURE:
<223> OTHER INFORMATION: 2 glucose inducible regulatory elements

<400> SEQUENCE: 9
cacgtggtgg ccacgtgctt gggcacgcca gttctcacgt ggtggccacg tg            52

<210> SEQ ID NO 10
<211> LENGTH: 91
<212> TYPE: DNA
<213> ORGANISM: Artificial
<220> FEATURE:
<223> OTHER INFORMATION: 3 glucose inducible regulatory elements

<400> SEQUENCE: 10
cacgtggtgg ccacgtgctt gggcacgcca gttctcacgt ggtggccacg tgcttgggca    60
cgaattccag ttctcacgtg gtggccacgt g                                   91

<210> SEQ ID NO 11
<211> LENGTH: 598
```

```
<212> TYPE: DNA
<213> ORGANISM: Artificial
<220> FEATURE:
<223> OTHER INFORMATION: 1 glucose inducible regulatory element fused to
      rat albumin promoter and 5' untranslated region and human insulin

<400> SEQUENCE: 11
gcggccgcca gttctcacgt ggtggccacg tgcttgggca cgaattctct agagggattt      60
agttaaacaa cttttttttt tcttttttggc aaggatggta tgattttgta atggggtagg    120
aaccaatgaa atgaaaggtt agtgtggtta atgatctaca gttattggtt agagaagtat    180
attagagcga gtttctctgc acacagacca cctttcctgt caacccactg cctctggcac    240
aatggccctg tggatgcgcc tcctgcccct gctggcgctg ctggccctct ggggacctga    300
cccagccgca gcctttgtga accaacacct gtgcggctca cacctggtgg aagctctcta    360
cctagtgtgc ggggaacgag gcttcttcta cacacccagg accaagcggg aggcagagga    420
cctgcaggtg gggcaggtgg agctgggcgg gggccctggt gcaggcagcc tgcagccctt    480
ggccctggag gggtcccggc agaagcgtgg cattgtggaa caatgctgta ccagcatctg    540
ctccctctac cagctggaga actactgcaa ctagacgcag cctgcaggca gcgtcgac      598

<210> SEQ ID NO 12
<211> LENGTH: 633
<212> TYPE: DNA
<213> ORGANISM: Artificial
<220> FEATURE:
<223> OTHER INFORMATION: 2 glucose inducible regulatory elements fused
      to rat albumin
      promoter and 5' untranslated region and human insulin

<400> SEQUENCE: 12
gcggccgcca gttctcacgt ggtggccacg tgcttgggca cgccagttct cacgtggtgg     60
ccacgtgctt gggcacgaat tctctagagg gatttagtta aacaactttt ttttttcttt   120
ttggcaagga tggtatgatt ttgtaatggg gtaggaacca atgaaatgaa aggttagtgt   180
ggttaatgat ctacagttat tggttagaga agtatattag agcgagtttc tctgcacaca   240
gaccaccttt cctgtcaacc cactgcctct ggcacaatgg ccctgtggat gcgcctcctg   300
cccctgctgg cgctgctggc cctctgggga cctgacccag ccgcagcctt tgtgaaccaa   360
cacctgtgcg gctcacacct ggtggaagct ctctacctag tgtgcgggga acgaggcttc   420
ttctacacac ccaggaccaa gcgggaggca gaggacctgc aggtggggca ggtggagctg   480
ggcgggggcc ctggtgcagg cagcctgcag cccttggccc tggaggggtc ccggcagaag   540
cgtggcattg tggaacaatg ctgtaccagc atctgctccc tctaccagct ggagaactac   600
tgcaactaga cgcagcctgc aggcagcgtc gac                                 633

<210> SEQ ID NO 13
<211> LENGTH: 666
<212> TYPE: DNA
<213> ORGANISM: Artificial
<220> FEATURE:
<223> OTHER INFORMATION: 3 glucose inducable regulatory elements fused
      to rat albumin promoter and 5' untranslated region and human
      insulin

<400> SEQUENCE: 13
gcggccgcca gttctcacgt ggtggccacg tgcttgggca cgccagttct cacgtggtgg     60
ccacgtgctt gggcacgaat tccagttctc acgtggtggc cacgtgcttg gcactctag    120 agggatttag ttaaacaact tttttttttc ttttggcaa ggatggtatg attttgtaat    180
```

```
ggggtaggaa ccaatgaaat gaaaggttag tgtggttaat gatctacagt tattggttag    240
agaagtatat tagagcgagt ttctctgcac acagaccacc tttcctgtca acccactgcc    300
tctggcacaa tggccctgtg gatgcgcctc ctgcccctgc tggcgctgct ggccctctgg    360
ggacctgacc cagccgcagc ctttgtgaac caacacctgt gcggctcaca cctggtggaa    420
gctctctacc tagtgtgcgg ggaacgaggc ttcttctaca cacccaggac caagcgggag    480
gcagaggacc tgcaggtggg gcaggtggag ctgggcgggg ccctggtgc aggcagcctg     540 cagcccttgg ccctggaggg gtcccggcag aagcgtggca ttgtggaaca atgctgtacc    600
agcatctgct ccctctacca gctggagaac tactgcaact agacgcagcc tgcaggcagc    660
gtcgac                                                                666
```

```
<210> SEQ ID NO 14
<211> LENGTH: 82
<212> TYPE: DNA
<213> ORGANISM: Artificial
<220> FEATURE:
<223> OTHER INFORMATION: glucose inducible regulatory element from rat
      S14 gene

<400> SEQUENCE: 14
gcggccgcca gttctcacgt ggtggccacg tgcttgggca cgccagttct cacgtggtgg    60
ccacgtgctt gggcacgtta ac                                              82
```

```
<210> SEQ ID NO 15
<211> LENGTH: 64
<212> TYPE: DNA
<213> ORGANISM: Artificial
<220> FEATURE:
<223> OTHER INFORMATION: synthetic oligonucleotide

<400> SEQUENCE: 15
ggggtaccga ccacctttcc tgtcaaccca ctgcctctgg cacaatggcc ctgtggatgc    60
gcct                                                                  64
```

```
<210> SEQ ID NO 16
<211> LENGTH: 30
<212> TYPE: DNA
<213> ORGANISM: Artificial
<220> FEATURE:
<223> OTHER INFORMATION: synthetic oligonucleotide

<400> SEQUENCE: 16
cggagtcgac ctagttgcag tagttctcca                                      30
```

```
<210> SEQ ID NO 17
<211> LENGTH: 30
<212> TYPE: DNA
<213> ORGANISM: Artificial
<220> FEATURE:
<223> OTHER INFORMATION: synthetic oligonucleotide

<400> SEQUENCE: 17
cggagtcgac gctgcctgca ggctgcgtct                                      30
```

```
<210> SEQ ID NO 18
<211> LENGTH: 4
<212> TYPE: PRT
<213> ORGANISM: Artificial
<220> FEATURE:
<223> OTHER INFORMATION: amino acid sequence of the C-A junction of wild
``` type human insulin

<400> SEQUENCE: 18

Leu Gln Lys Arg
1

<210> SEQ ID NO 19
<211> LENGTH: 4
<212> TYPE: PRT
<213> ORGANISM: Artificial
<220> FEATURE:
<223> OTHER INFORMATION: amino acid sequence of the C-A junction of
      mutant human insulin

<400> SEQUENCE: 19

Arg Gln Lys Arg
1

<210> SEQ ID NO 20
<211> LENGTH: 31
<212> TYPE: DNA
<213> ORGANISM: Artificial
<220> FEATURE:
<223> OTHER INFORMATION: oligonucleotide corresponding to human insulin

<400> SEQUENCE: 20
ccaggaccaa gcgggaggca gaggacctgc a                              31

<210> SEQ ID NO 21
<211> LENGTH: 35
<212> TYPE: DNA
<213> ORGANISM: Artificial
<220> FEATURE:
<223> OTHER INFORMATION: oligonucleotide corresponding to human insulin

<400> SEQUENCE: 21
tgcctcccgc ttggtcctgg gtgtgtagaa gaagc                          35

<210> SEQ ID NO 22
<211> LENGTH: 4
<212> TYPE: PRT
<213> ORGANISM: Artificial
<220> FEATURE:
<223> OTHER INFORMATION: amino acid sequence of the B-C junction of wild
      type human insulin

<400> SEQUENCE: 22

Lys Thr Arg Arg
1

<210> SEQ ID NO 23
<211> LENGTH: 4
<212> TYPE: PRT
<213> ORGANISM: Artificial
<220> FEATURE:
<223> OTHER INFORMATION: amino acid sequence of the B-C junction of
      mutant human insulin

<400> SEQUENCE: 23

Arg Thr Lys Arg
1

<210> SEQ ID NO 24
<211> LENGTH: 206
<212> TYPE: DNA
<213> ORGANISM: Artificial
<220> FEATURE:

<223> OTHER INFORMATION: rat albumin promoter sequence

<400> SEQUENCE: 24

```
gggatttagt taaacaactt ttttttttct ttttggcaag gatggtatga ttttgtaatg     60
gggtaggaac caatgaaatg aaaggttagt gtggttaatg atctacagtt attggttaga    120
gaagtatatt agagcgagtt tctctgcaca cagaccacct ttcctgtcaa cccactgcct    180
ctggcacaat gaagtgggta accttt                                         206
```

<210> SEQ ID NO 25
<211> LENGTH: 829
<212> TYPE: DNA
<213> ORGANISM: Artificial
<220> FEATURE:
<223> OTHER INFORMATION: insulin gene expression cassette

<400> SEQUENCE: 25

```
gcggccgcca gttctcacgt ggtggccacg tgcttgggca cgccagttct cacgtggtgg     60
ccacgtgctt gggcacgaat tccagttctc acgtggtggc cacgtgcttg ggcactctag    120
agggatttag ttaaacaact tttttttttc ttttggcaa ggatggtatg attttgtaat     180
ggggtaggaa ccaatgaaat gaaaggttag tgtggttaat gatctacagt tattggttag    240
agaagtatat tagagcgagt ttctctgcac acagaccacc tttcctgtca acccactgcc    300
tctggtacca gcgcagaggc ttgggcagc cgagcggcag ccaggccccg gcccgggcct     360
cggttccaga agggagagga gcccgccaag gcgcgcaaga gagcgggctg cctcgcagtc    420
cgagccggag agggagcgcg agccgcgccg gccccggacg gcctccgaaa ccatggccct    480
gtggatgcgc ctcctgcccc tgctggcgct gctggccctc tggggacctg acccagccgc    540
agcctttgtg aaccaacacc tgtgcggctc acacctggtg gaagctctct acctagtgtg    600
cggggaacga ggcttcttct acacacccag gaccaagcgg gaggcagagg acctgcaggt    660
ggggcaggtg gagctgggcg ggggccctgg tgcaggcagc ctgcagccct ggccctggga    720
ggggtcccgg cagaagcgtg gcattgtgga acaatgctgt accagcatct gctccctcta    780
ccagctggag aactactgca actagacgca gcctgcaggc agcgtcgac                829
```

<210> SEQ ID NO 26
<211> LENGTH: 19
<212> TYPE: DNA
<213> ORGANISM: Artificial
<220> FEATURE:
<223> OTHER INFORMATION: synthetic oligonucleotide

<400> SEQUENCE: 26

```
gtcaacccac tgcctctgg                                                  19
```

<210> SEQ ID NO 27
<211> LENGTH: 19
<212> TYPE: DNA
<213> ORGANISM: Artificial
<220> FEATURE:
<223> OTHER INFORMATION: synthetic oligonucleotide

<400> SEQUENCE: 27

```
tgcaggctgc gtctagttg                                                  19
```

<210> SEQ ID NO 28
<211> LENGTH: 20
<212> TYPE: DNA
<213> ORGANISM: Artificial

```
<220> FEATURE:
<223> OTHER INFORMATION: synthetic oligonucleotide

<400> SEQUENCE: 28
ctgcccaggc ttttgtcaaa                                              20

<210> SEQ ID NO 29
<211> LENGTH: 20
<212> TYPE: DNA
<213> ORGANISM: Artificial
<220> FEATURE:
<223> OTHER INFORMATION: synthetic oligonucleotide

<400> SEQUENCE: 29
tattcattgc agaggggtgg                                              20

<210> SEQ ID NO 30
<211> LENGTH: 18
<212> TYPE: DNA
<213> ORGANISM: Artificial
<220> FEATURE:
<223> OTHER INFORMATION: synthetic oligonucleotide

<400> SEQUENCE: 30
tcgtgccaaa aagggccg                                                18

<210> SEQ ID NO 31
<211> LENGTH: 23
<212> TYPE: DNA
<213> ORGANISM: Artificial
<220> FEATURE:
<223> OTHER INFORMATION: synthetic oligonucleotide

<400> SEQUENCE: 31
gctccttaca tgggctttgg tgg                                          23
```

TREATMENT OF DIABETES WITH SYNTHETIC BETA CELLS

CROSS-REFERENCE TO RELATED APPLICATIONS

This application is a continuation-in-part of U.S. Ser. No. 10/923,924 filed Aug. 23, 2004, now abandoned; which is a continuation of U.S. Ser. No. 10/013,032 filed Nov. 12, 2001, now U.S. Pat. 6,933,133; which is continuation of U.S. Ser. No. 09/537,696 filed Mar. 28, 2000 issued as U.S. Pat. No. 6,352,857; which is a continuation-in-part of application Ser. No. 09/115,888, filed Jul. 15, 1998 now abandoned, which is a continuation-in-part of application Ser. No. 08/786,625 filed Jan. 21, 1997, now abandoned. All applications and patents are incorporated by reference.

STATEMENT REGARDING FEDERALLY SPONSORED RESEARCH OR DEVELOPMENT

This invention was made with United States government support awarded by NIH, Grant Nos: R01 DK35446-09 and R01 DK49545-01. The United States government has certain rights in this invention.

BACKGROUND OF THE INVENTION

This invention relates to treatment of diabetes with synthetic beta cells, and specifically to a method of utilizing non-islet cells comprising a genetic construct that has a coding sequence for a proinsulin expressible in the cells in response to glucose levels. The proinsulin synthesized in the cells is further processed into a secretable, active insulin.

Insulin is normally produced in and secreted by the beta cells of the islets of Langerhans in the pancreas. Mature insulin is a protein having two polypeptide chains, A and B, held together by disulfide bonds. The glucose responsive release of insulin from the beta cells is a complex event including gene expression, posttranslational modification and secretion. The initial protein product and insulin precursor is preproinsulin, a single polypeptide chain having an N-terminal signal sequence and an intervening sequence, the C-peptide, between the A and B chains. The signal sequence is cleaved during transport from the rough endoplasmic reticulum to form proinsulin. The proinsulin is packaged into secretory granules along with specific enzymes required for its processing. Proinsulin folds into a specific three-dimensional structure, forming disulfide bonds. Mature insulin results from removal of the C-peptide. In beta cells, this function is catalyzed by endopeptidases that recognize the specific amino acid sequences at the junction of the A chain and the C peptide (C-A junction) and at the junction of the B chain and the C peptide (B-C junction). Mature insulin, stored in secretory granules, is released in response to elevated blood glucose levels. The detailed mechanism of insulin release is not completely understood, but the process involves migration to and fusion of the secretory granules with the plasma membrane prior to release.

In normally functioning beta cells, insulin production and release is affected by the glycolytic flux. Glucokinase and glucose transporter 2 (GLUT-2) are two proteins that are believed to be involved in sensing changes in glucose concentration in beta cells. A reduction in GLUT-2, which is involved in glucose transport, is correlated with decreased expression of insulin; loss of glucokinase activity causes a rapid inhibition of insulin expression.

Autoimmune destruction of pancreatic beta cells causes insulin-dependent diabetes mellitus or Type I diabetes. As a consequence of partial or complete loss of beta cells, little or no insulin is secreted by the pancreas. Most cells, with the exception of brain cells, require insulin for the uptake of glucose. Inadequate insulin production causes reduced glucose uptake and elevated blood glucose levels. Both reduced glucose uptake and high blood glucose levels are associated with a number of very serious health problems. In fact, without proper treatment, diabetes can be fatal.

One conventional treatment for diabetes involves periodic administration of injectable exogenous insulin. This method has extended the life expectancy of millions of people with the disease. However, blood glucose levels must be carefully monitored to ensure that the individual receives an appropriate amount of insulin. Too much insulin, can cause blood glucose levels to drop to dangerously low levels. Too little insulin will result in elevated blood glucose levels. Even with careful monitoring of blood glucose levels, control of diet, and insulin injections, the health of the vast majority of individuals with diabetes is adversely impacted in some way.

Replacement of beta cell function is a treatment modality that may have certain advantages over insulin administration, because insulin would be secreted by cells in response to glucose levels in the microenvironment. One way of replacing beta cell function is by pancreas transplantation, which has met with some success. However, the supply of donors is quite limited, and pancreas transplantation is very costly and too problematic to be made widely available to those in need of beta cell function.

There have been many other proposed alternatives for beta cell replacement, including replacing beta cell function with actual beta cells or other insulin-secreting, pancreas-derived cell lines (Lacy, et al., *Ann. Rev. Med.*, 37:33, 1986). Because the immune system recognizes heterologous cells as foreign, the cells have to be protected from immunoactive cells (e.g., T-cells and macrophages mediating cytolytic processes). One approach to protect heterologous cells is physical immunoisolation; however, immunoisolation itself poses significant problems.

U.S. Pat. No. 5,427,940 issued to Newgard discloses another approach to beta cell replacement. This patent describes an artificial beta cell produced by engineering endocrine cells of the At-T-20 ACTH secreting cells. A stably transfected cell, At-T-20, is obtained by introducing cDNA encoding human insulin and the glucose transporter gene, i.e. the GLUT-2 gene, driven by the constitutive CMV promoter. The cell line already expresses the correct isoform of glucokinase required for glucose responsive expression of the proinsulin gene. Although the cell line is responsive to glucose, it is secretagogue-regulated at concentrations below the normal physiological range. Therefore, use of these cells in an animal would likely cause chronic hypoglycemia; furthermore, these cells are derived from a heterologous source and bear antigens foreign to the recipient host.

U.S. Pat. No. 5,534,404 issued to Laurance et al. discloses another approach to obtaining a cell line in which insulin production is secretagogue-regulated. Subpopulations of beta-TC-6 cells having an increased internal calcium concentration, a property associated with insulin secretion, were selected using a cell sorter. After successive passages, a subpopulation of cells that produce insulin in response to glucose in the physiological range (4-10 mM) was selected, and the cells were encapsulated for therapeutic use in alginate bounded by a PAN/PVC permselective hollow fiber membrane according to the method of Dionne (International Patent application No. PCT/US92/03327).

Valera, et al., *FASEB Journal*, 8: 440 (1994) describes transgenic mouse hepatocytes expressing insulin under the control of the PEPCK promoter driven by P-enolpyruvate. The PEPCK promoter is sensitive to the glucagon/insulin ratio and is activated at elevated glucose levels. The PEPCK/insulin chimeric gene was introduced into fertilized mouse eggs. Under conditions of severe islet destruction by streptozotocin (SZ), the production and secretion of intact insulin by the liver compensated for loss of islet function.

Despite these prior art attempts, there is a continuing need for alternative methods to conventional insulin therapy for the treatment of diabetes.

SUMMARY OF THE INVENTION

The present invention relates to a genetic construct that can be used to obtain glucose-inducible expression of active insulin in a host cell. The genetic construct permits glucose-regulated expression of proinsulin in the presence of higher than physiologic concentrations of glucose, but not at lower than physiologic glucose concentrations. The present invention further provides that the proinsulin encoded by the coding sequence of the genetic construct comprises an amino acid sequences that allows the proinsulin to be converted into a secretable, active insulin.

In one aspect, the invention provides a genetic construct for glucose-inducible expression of active insulin in host cells. The construct comprises (i) a coding sequence for a human proinsulin, the coding sequence operably connected a promoter functional in the host cell, wherein the proinsulin amino acid sequences corresponding to the B-C and C-A junctions of native human proinsulin are cleavable in the host cell; (ii) a glucose responsive regulatory module located 5' of the promoter, the module having at least one glucose inducible regulatory element (GIRE) comprising a pair of CACGTG motifs linked by a five base nucleotide sequence; and (iii) a 5' untranslated region (UTR), located 5' of the coding sequence and 3' of the promoter, not natively associated with the coding sequence for human proinsulin. A highly advantageous feature of the invention is that a 5' UTR not natively associated with the human proinsulin coding sequence is employed to reduce the formation of secondary structures that can lead to translational pausing and reduced expression of preproinsulin.

In another aspect, the invention includes a method for obtaining glucose-regulated expression of active insulin in a mammalian subject, comprising the step of delivering into the subject a genetic construct according to the invention in an amount and under conditions effective to allow at least a portion the subject's cells to take up the construct. In a preferred embodiment, the genetic construct is integrated into the genome of a suitable virus-derived vector infective for a target host cell for delivery into the subject.

In another aspect, the invention provides a method for regulating blood glucose levels wherein insulin is secreted in response to glucose levels by cells transformed by the aforementioned genetic construct.

In another aspect, the present invention includes the genetic construct described above additionally comprising a transcriptional enhancer.

Other advantages and a fuller appreciation of specific features of the invention will be gained upon review of the following drawings and detailed descriptions of preferred embodiments.

BRIEF DESCRIPTION OF THE DRAWINGS

FIGS. 11A and 11B is (A) a construction of 3SATEM insulin gene expression cassettes and (B) the nucleotide sequence of the 3SATEM cassette. Referring to FIG. 11B, residues 1-121 bp: Gires with Not I and Xba I sites on 5'-3'-end, respectively; residues 122-309 bp: albumin promoter, Kpn I site on 3'-end; italicized letters; residues 310-472 bp: translation enhancer (TE) from VEGF, lower case letters; and residues 472-829 bp: human insulin cDNA modified for post-translational proteolytic compatibility with Furin (3'-end carries SalI site).

FIG. 12: Freshly isolated primary rat hepatocytes were transfected with equal amount of adenovirus containing either SAM or SATEM, as indicated. Transfected cells were exposed to either 3.5 mM or 27.5 mM glucose for the indicated period of time. A minimum of four cell culture plates were employed for each construct at each indicated glucose concentration and the experiment was repeated more than three times; secreted insulin was measured in the medium by ELISA, as described in the text.

FIG. 13A: Each group consisted of 6 STZ-diabetic rats and treated with identical amount of adeno-virus vector containing the indicated gene construct. Blood glucose levels were recorded after 3 hour, 6 hour, and 9 hour fast; the data for 9 hour fast are shown here. Lowering in blood glucose levels of Ad.SATEM treated diabetic animals was statistically significant when compared to those treated with Ad.3SAM2 ($p<0.05$) after 3, 6, and 9 hour fasting and after a 9 hour fast glucose levels in Ad.SATEM treated animals were statistically indistinguishable from those of non-diabetic control. FIG. 13B: Treatment of diabetic rats with both insulin constructs caused stabilization in further reduction of body weight. Although, there was a tendency of Ad.SATEM treatment to stabilize the weight of diabetic rats better, the difference between Ad.3SAM2 and Ad.SATEM treatments was not significant but both treatments caused a significant difference when compared to the untreated diabetic rats.

DETAILED DESCRIPTION OF THE PREFERRED EMBODIMENT

Figure 1:
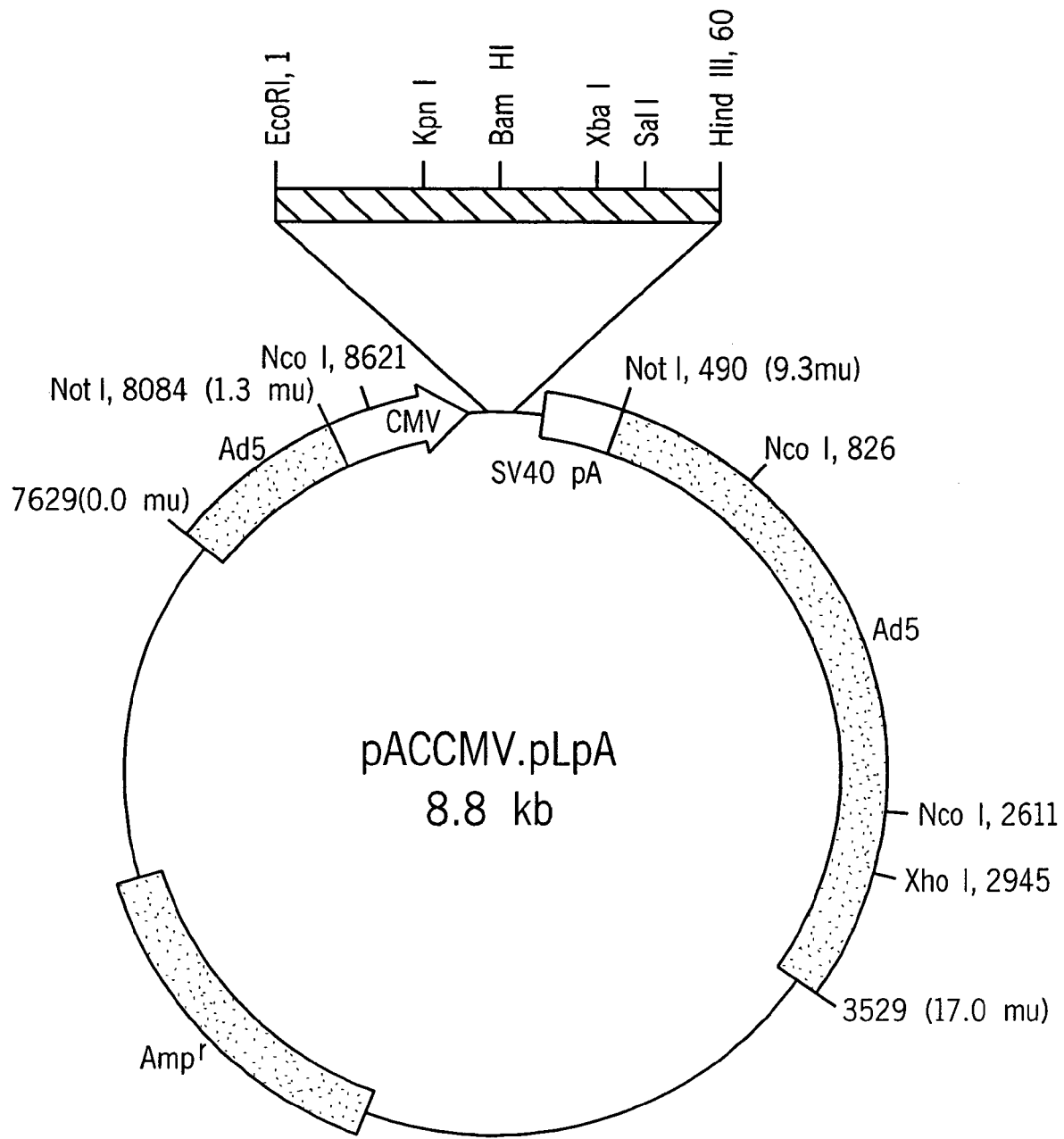
FIG. 1 is a genetic map of the pACCMV.plpA, an 8.8 kb plasmid containing the cloning sites for the expression construct for proinsulin, and also several adenoviral genes.
Figure 2A:
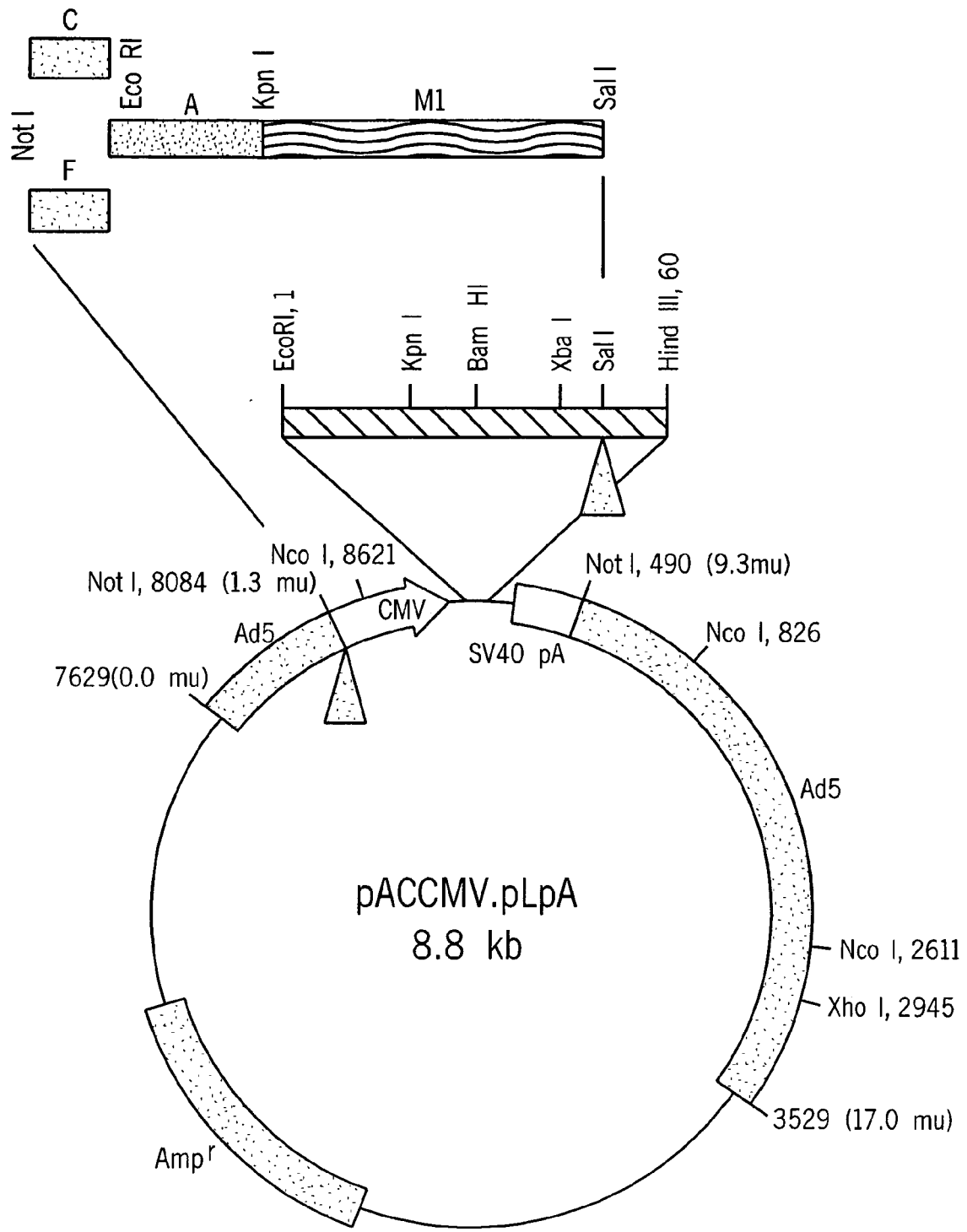
FIG. 2A is a genetic map showing the insertion of the expression construct in relation to various markers on the pACCMV.p.A plasmid.
Figure 2B:
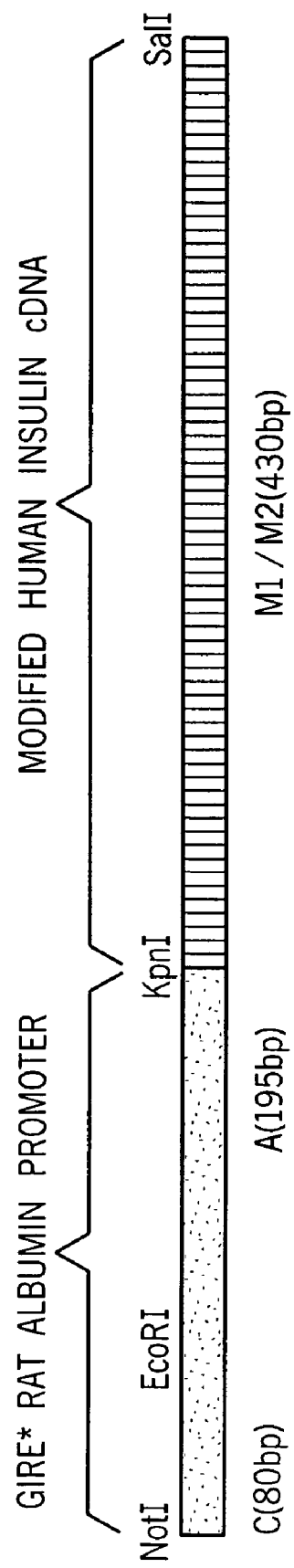
FIG. 2B shows the order of genetic elements 5' to 3'.
Figure 3:
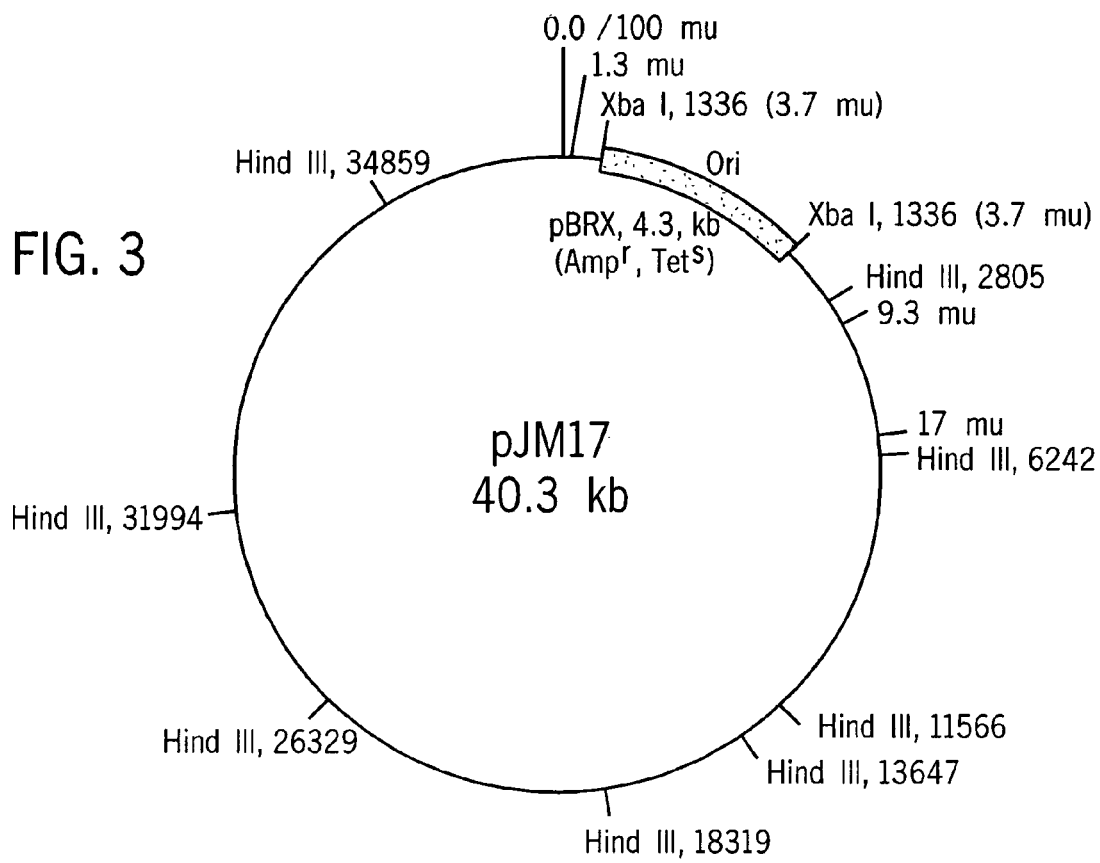
FIG. 3 is a genetic map of pJM17.
Figure 4:
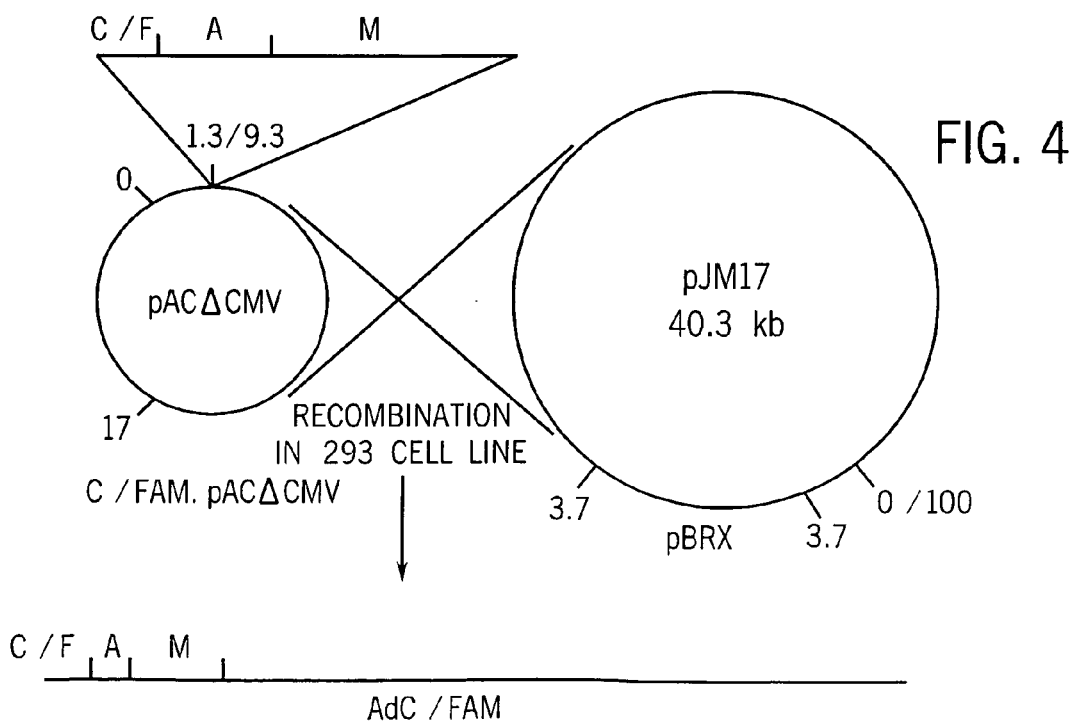
FIG. 4 is a genetic map showing the recombination of vectors pACCMV.plpA and pJM17 to yield the AdC/FAM construct.

The present invention provides a method for producing insulin in a cell in which insulin is not natively produced, comprising delivering into the cell a genetic construct comprising a nucleotide coding sequence expressible in the cells in response to increased glucose concentrations, the sequence encoding a proinsulin that can be processed into active insulin in the host cell. Accordingly, one aspect of the invention is a genetic construct containing a nucleotide sequence encoding proinsulin operably connected to a promoter functional in the host cell under control of one or more glucose inducible regulatory elements (GIRE), which confer glucose-regulated control of transcription of the sequence. Specifically, the construct in accordance with the present invention includes (i) a promoter functional in the host cell; (ii) a coding sequence for a human proinsulin, the coding sequence operably connected to the promoter, and wherein the proinsulin amino acid sequences corresponding to the B-C and C-A junctions of native human proinsulin are cleavable in the host cell; (iii) a glucose responsive regulatory module located 5' of the promoter, the module having at least one GIRE comprising a pair of CACGTG motifs linked by a five base sequence; and (iv) a 5' untranslated region (UTR), located 5' of the coding sequence, not natively associated with the coding sequence for human proinsulin.

By a "coding sequence for human proinsulin," it is meant a sequence that encodes an insulin precursor capable of being processed into a protein having the biological activity of insulin ("active insulin"). As used herein, "active insulin" is a protein, the in vivo expression of which is correlated with a reduction in blood glucose levels. The coding sequences disclosed in the Examples herein encode preproinsulin, which includes a signal peptide that is important in the transit of the nascent polypeptide. However, for the sake of simplicity, a "coding sequence for human proinsulin" will be used throughout, because the signal peptide is removed from preproinsulin during or very shortly after translation to form proinsulin.

In the Examples below, hepatocytes and Cos7 cells were used to evaluate the glucose-inducible expression of a proinsulin coding sequence under the control of a glucose responsive regulatory module. Hepatocytes were chosen as a candidate for glucose-regulated expression of insulin because hepatocytes contain GLUT-2 and glucokinase, enzymes believed important in glucose "sensing." However, it is reasonably expected that other cell types may also be suitable in the practice of the present invention.

Another advantage of using hepatocytes for insulin production is that these cells contain the endopeptidase furin. Furin is believed to cleave proinsulin at its B-C junction, although it is very inefficient at cleaving the C-A junction. As explained hereinbefore, cleavage at both sites is necessary for excision of the C-peptide, which is required for conversion of proinsulin to active insulin. A single point mutation ($T^{257}$ to G) in the human insulin open reading frame (ORF) converts the amino acid sequence LQKR (SEQ ID NO:18) to RQKR (SEQ ID NO:19), which results in a modified C-A junction that can be cleaved by furin. Thus, the proinsulin protein can be processed into insulin in cells having an endopeptidase capable of cleaving the modified C-A junction, i.e. insulin (M1).

As described in the Examples below, modification of the coding region for human insulin specifying the B-C junction of native insulin converts the amino acid sequence of proinsulin KTRR (SEQ ID NO:22) to a cleavable B-C junction having a different sequence RTKR (SEQ ID NO:23) i.e. insulin (M2). Modification of both junctions, C-A and B-C, facilitates conversion of proinsulin to active insulin.

In the Examples, various combinations of different glucose inducible regulatory elements were constructed and evaluated for their ability to allow glucose-induced transcription of insulin mRNA. As used herein, a "glucose inducible regulatory element" (GIRE) refers to a polynucleotide sequence containing at least one pair of perfect CACGTG motifs, each member of the pair separated from the other by a sequence of five base pairs. A "glucose responsive regulatory module" contains one or more GIREs. The regulatory elements were inserted 5' of the 5' untranslated region of human proinsulin gene and then cloned into an adenovirus vector which was used to transfect hepatocytes. As the Examples below demonstrate, the GIREs provide transcriptional regulation of insulin mRNA in hepatocytes in response to physiologically relevant glucose concentrations.

In the Examples below, a rat albumin promoter was used as the promoter in the tested constructs (SEQ ID NO:24). However, any suitable promoter that is functional in the intended target cell could be employed. The promoter is preferably a relatively strong constitutive promoter operative in the host cell of choice, and responsive to the regulatory module located on its 5' end.

The 5'-untranslated region (5'-UTR) of the human proinsulin gene contains an inverted repeat capable of forming a stem-loop in the insulin mRNA, the formation of which inhibits translation. To minimize reduced translation by formation of secondary structures caused by intramolecular base-pairing of the 5' UTR, the 5'-UTR of the proinsulin gene was replaced with the 5'-UTR of rat albumin (bases 153-188 of the sequence published as GenBank Accession No. M16825, SEQ ID No:24) in its native orientation. Those skilled in art will appreciate that other 5'-UTRs may be substituted for the rat albumin 5'-UTR. It is important that adequate spacing (about 25 base pairs) be provided between the regulatory module and the transcriptional start site, and that the 5' UTR does not result in secondary structure that will interfere with binding to and processing by ribosomes.

The 3'-UTR of human preproinsulin affects the half life of mRNA, and hence, the production of protein over time. Two different constructs were prepared to include the rat albumin 5'-UTR (bases 153-188 of GenBank Accession No. M16825; SEQ ID NO:24), a human insulin ORF, and varying lengths of 3'-UTR. Two constructs, designated M2A and M2B, differ only in that M2A terminates at the stop codon of the open reading frame, whereas M2B contains an additional 18 bases after the stop codon in the 3'UTR of human proinsulin. The two constructs M2A and M2B were used to evaluate insulin expression in Cos7 host cells.

Insulin production was compared from constructs containing regulatory modules having one (SEQ ID NO:8), two (SEQ ID NO:9) or three (SEQ ID NO:10) GIRES in combination with the rat albumin promoter, rat albumin 5' UTR and proinsulin sequence M2B. The complete sequences of these constructs, which were inserted into adenovirus vectors, are listed as SEQ ID NO:11, SEQ ID NO:12, and SEQ ID NO:13, respectively. Hepatocytes transfected with the adenovirus vector containing a regulatory module having one GIRE demonstrated relatively low levels of insulin production, whereas hepatocytes transfected with the vectors having regulatory modules containing two or more GIREs demonstrated high levels of insulin production in response to physiologically relevant levels of glucose. It is expected that the baseline production of insulin will plateau with increasing numbers of GIREs. Furthermore, the construct containing a module with three GIREs was more responsive to 10 mM glucose than was the construct containing two GIREs.

The regulatory module for glucose-inducible transcription in the present invention is a synthetic oligonucleotide having at least one GIRE, each GIRE containing two operative regulatory motif segments CACGTG separated by a nucleotide linker segment, conveniently of the sequence GGCGC. Preferably, the regulatory module contains from 2 to 8 GIREs, and most preferably, the module contains from 3 to 5 GIREs. Additional GIREs are not expected to result in further increases in transcription. Moreover, GIREs in excess of five are not expected to interfere with glucose-inducible regulation.

One viral vector suitable for use in the method of the invention is a helper-free, replication-defective vector, derived from the adenovirus genome, and described in Newgard, et al., "Glucose-Regulated Insulin Secretion," in *Molecular Biology of Diabetes*, eds. Draznin, et al., Humana Press 1992. FIGS. 1-4 diagram the genetic components and construction of the vector containing the genetic construct. It is expected that other transducing systems may also be suitable for the present invention. For example, it is expected that the integrative retroviral systems and another helper-free recombinant adenoviral system disclosed in U.S. Pat. No. 5,436,146 issued to Shenk, et al. may be useful.

Viral-derived vectors have the advantage that delivery to target cells is relatively straightforward and can be accomplished in vivo. However, it should be appreciated that the constructs of the present invention could also be used to transfect cells ex vivo, which could then be reintroduced into a mammalian subject in vivo.

In in vivo studies, it was found that streptozotocin-treated (SZ) diabetic rats whose livers were injected with a viral vector containing the genetic construct in accordance with the present invention were able to control blood glucose levels comparable to normal rates, while untreated SZ-diabetic rats had blood glucose levels four fold higher than the treated SZ-diabetic and normal rats. It was also found that fasting blood glucose levels were significantly reduced in the SZ-diabetic rats compared to the untreated SZ-diabetic rats and that the blood glucose levels were reduced in a viral dose-dependent manner. As shown in the Examples, the level of blood glucose reduction in SZ-diabetic rats is a function of the dose of the viral vector delivered to the rat.

The viral dose employed in the Examples below was $1 \times 10^{12}$ or $2 \times 10^{12}$ pfu per rat. The virus was delivered in a phosphate buffered saline carrier. It is envisioned that the present invention may be practiced using different doses or carriers. It is well within the ability of one skilled in the art to determine optimal doses and to select suitable carriers. In the Examples below, the virus was delivered by direct injection into the liver. In addition to direct injections, the virus may be administered by delivery into an in-dwelling catheter placed in the hepatic portal vein.

In the Examples below, rats were used for in vivo studies. Rats are the preferred model system for studying diabetes in humans. It is reasonably expected that the present invention may be employed to obtain expression of insulin in diabetic humans as well.

It will be apparent to one skilled in the art that any structural gene for which glucose-modulated control is desired may be inserted into the gene construct using standard molecular biological techniques and expressed in a suitable host cell. The glucose regulatory module of the present invention may be used to prepare a genetic construct suitable for restoring glucose-mediated expression of proteins implicated in a number of metabolic diseases.

Figure 11A:
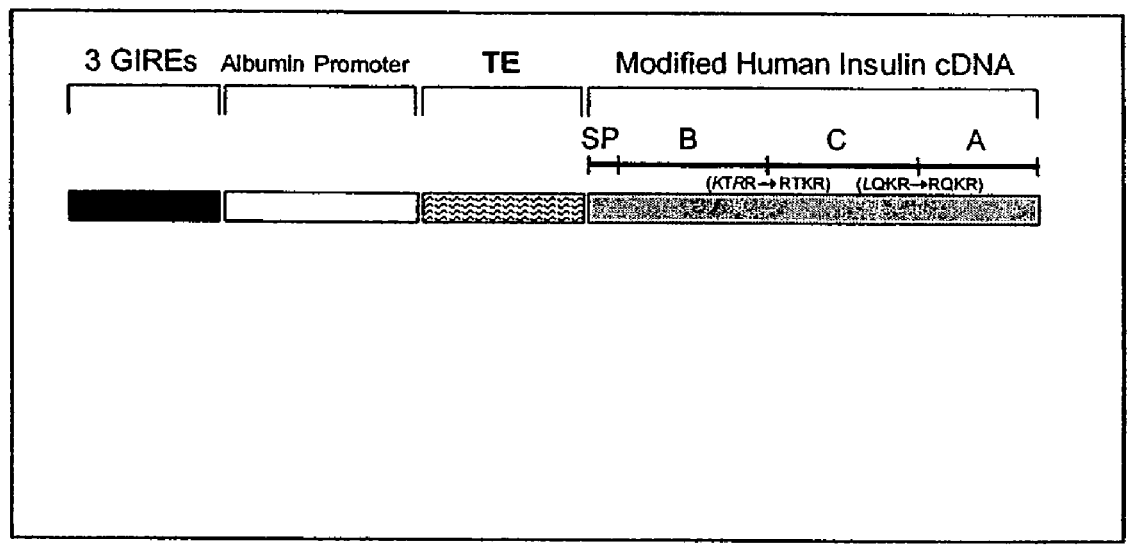

In another embodiment of the present invention, one would increase insulin output by generating a gene construct as described above additionally comprising a translational enhancer (TE) sequence. The Examples below show a preferred translational enhancer sequence derived from vascular endothelial growth factor (VEGF). FIG. 11 depicts this embodiment. FIG. 11A shows the translational enhancer relative to the GIREs, promoter, and human insulin coding sequence. FIG. 11B is a sequence listing of the entire construct. Nucleotides 310-472 are the VEGF translational enhancer.

The Examples below demonstrate that we have significantly increased insulin serum concentration under both post-prandial and fasting conditions by at least 3-fold. To be suitable for the present invention, a translational enhancer sequence must increase insulin serum concentration under either post-prandial or fasting conditions relative to a construct without TE sequences. Preferably TE sequences increase insulin production by 2-fold, more preferably by 3-4 fold and most preferably by 10-fold.

Other sequences suitable to further enhance insulin expression in the present invention include internal ribosomal entry sites (IRES), preferably from BiP, EGF, PDGF-B, IGF-II, and eIF4G. For example, a general reference for IRES is Paulous, S., et al., "Comparison of the capacity of different viral internal ribosome entry segments to direct translation initiation in poly(A)-dependent reticulocyte lysates," *Nucleic Acids Res.* 31(2):722-33, 2003, which is herein incorporated by reference. One of skill would review the following references, incorporated by reference, to obtain suitable IRES:

| | |
|---|---|
| BiP | Yang, Q. and Sarnow, P., "Location of the internal ribosome entry site in the 5' non-coding region of the immunoglobulin heavy-chain binding protein (BiP) mRNA: evidence for specific RNA-protein interactions," Nucleic Acids Res. 25(14): 2800-2807, 1997. |
| IGF-II | Pedersen, S. K., et al., "Human insulin-like growth factor II leader 2 mediates internal initiation of translation," Biochem J. 363(Pt 1): 37-44, 2002. |
| eIF4G | Han, B. and Zhang, J. T., "Regulation of gene expression by internal ribosome entry sites or cryptic promoters: the eIF4G story," Mol. Cell Biol. 22(21): 7372-7384, 2002. |
| PDGF-B | Han, B., et al., "Tight control of platelet-derived growth factor B/c-sis expression by interplay between the 5'-untranslated region sequence and the major upstream promoter," J. Biol. Chem. 278(47): 46983-93, 2003. |

Preferably, the translational enhancement is in the 5'-UTR and more preferably in a position 3' of the promoter. The sequence will be operably connected to the promoter and coding DNA sequence, preferably as described in FIG. 11.

The following nonlimiting examples are intended to be purely illustrative.

EXAMPLES

Example 1

Isolation of Proinsulin Coding Sequences

Proinsulin cDNA was prepared by extracting total RNA from normal human islet cells, isolating the mRNA fraction and using it as a template to conduct an oligo $(dT)_{15}$ primed reverse transcription reaction. Insulin cDNA (−28 bp-443 bp) was amplified using sense and antisense oligonucleotides designated TA423 (SEQ ID NO:1) and TA413 (SEQ ID NO:2) which include restriction sites for KpnI and SalI, respectively. Alternatively, cDNA can be isolated according to the methods described in Bell, et al., Nature, 282:525 (1979), using the primers disclosed therein, but incorporating restriction sites compatible with the selected cloning vehicle.

The amplified cDNA fragment (−28 bp-443 bp) containing the entire coding sequence of human insulin and portions of the 5'-UTR and the 3'-UTR was subcloned into pBlueScript SK+ (Shon, et al., Nuc. Acids Res., 16: 7583, 1988).

Example 2

Amplification of Rat Albumin Promoter

A sequence comprising nucleotides 1-184 of the rat albumin (Heard, et al., Mol. Cell. Biol., 7: 2425-2434, 1987, incorporated herein by reference) was obtained by PCR amplification with synthetic primers using rat genomic DNA as the template DNA. The primers, which contain EcoRI and KpnI restriction sites, were designated TA420 (SEQ ID NO:6) and TA421 (SEQ ID NO:7). The amplified rat albumin promoter fragment was purified and incubated under suitable conditions with Kpn I and Eco RI, and ligated to linearized pBlueScript DNA having compatible ends. The sequence (SEQ ID NO:24) was verified by conventional sequencing techniques.

Example 3

Generation of a Mutant Insulin with Cleavable C-A and B-C Junctions

A mutation that changes the codon specifying Leu to a codon specifying Arg at position 62 was made using standard in vitro mutagenesis. The sense oligonucleotide TA403 (SEQ ID NO:3), which includes a point mutation corresponding to the desired change in the target region, and oligonucleotide TA413 (SEQ ID NO:2) were used as primers to amplify one segment of insulin sequence. Similarly, an antisense oligonucleotide TA404 (SEQ ID NO:4) containing the Leu to Arg mutation was used with the original insulin sense oligonucleotide TA423 (SEQ ID NO:1) to amplify the second fragment of modified insulin (MI). The two fragments thus produced were purified, combined, and used as template DNA to amplify the modified insulin M1 using oligonucleotides TA423 and TA413 as primers. The C-A modified insulin M1 was ligated to pBlueScript SK+, linearalized with KpnI and SalI, or used as a template for generating a second mutant containing a mutation in the B-C junction. Using primers TA414 (SEQ ID NO:20) and TA415 (SEQ ID NO:21), the insulin M1 sequence was subjected to in vitro mutagenesis to obtain mutations in the coding region specifying the B-C junction (KTRR; SEQ ID NO:22) to obtain a sequence that encodes a B-C junction having the sequence RTKR (SEQ ID NO:23), i.e. insulin (M2).

Example 4

Generation and Cloning of Proinsulin Genetic Constructs in the Plasmid pACdeltaCMV The plasmid pACCMV.pLpA (FIG. 1) was used as a vector for generation of replication defective recombinant adenovirus containing genes of interest. The CMV promoter was removed by digesting plasmid DNA with SalI and partially digesting the DNA with the enzyme NotI. The 8.3 kb piece of vector DNA (pACdeltaCMV) lacking the CMV promoter was isolated by agarose gel electrophoresis and by gel purification.

Constructs containing either the C or F module were prepared. The C module (SEQ ID NO:14) is based on the published sequence of S14 (Shih & Towle, J. Biol. Chem. 269: 9380-9387, 1994). The F module (SEQ ID NO:5) is found in the fatty acid synthetase gene. An oligonucleotide pair corresponding to a glucose responsive regulatory module C or F was combined with gel purified EcoRI-KpnI rat albumin promoter and Kpni-SalI InsMI DNA fragments, and ligated into the above-described plasmid vector pACdeltaCMV. Two different constructs containing either module C or module F were obtained. Each of the two constructs was co-transfected with the plasmid pJM17 into the host HEK 293 cell line to generate recombinant replication-defective adenovirus constructs, namely AdCAMI and AdFAMI (see FIG. 5).

Example 5

Expression of Insulin in Hepatocytes at Various Glucose Concentrations

Rat hepatocytes were prepared by in situ perfusion of 0.5 mg/mL collagenase in supplemented balanced Hank's solution as described in Kreamer, et al., In Vitro 22:201-211, 1986. The viability of isolated hepatocytes was 90% or higher.

Six collagen coated 60 mm plates, each containing $1\times10^6$ hepatocytes, were transfected with AdCAMI or AdFAMI ($5\times10^7$ pfu/plate). Transfected hepatocytes were exposed to three concentrations of glucose, 3.3 mM, 5.6 mM and 27.5 mM, in RPMI supplemented with 10% fetal calf serum, 30 µg/mL proline, 5 µg/mL insulin, 5 µg/mL transferrin and 5 µg/mL selenium, and incubated at 37° C. After 36 hours, RNA was isolated from hepatocytes on one of two plates used at each tested glucose concentration. The duplicate plate was used to evaluate cell viability. Variation in hepatocyte viability of cells exposed to different concentrations of glucose was less than 10%.

10 µg of RNA from each sample was separated electrophoretically on a formaldehyde-2% agarose gel, transferred to a Nylon membrane, UV-crosslinked, and hybridized with digoxygenin-labeled insulin cRNA. Detection of the membrane-bound probe was performed by chemiluminescence. The results were recorded as multiple exposures on X-ray films for various lengths of time and quantitated by digital image analysis.

Northern analysis revealed an intense signal migrating at the position predicted by the size of the proinsulin transcript (1.35 kb). This band was observed only in transfuced hepatocytes cultured in the presence of 27.5 mM glucose. There appeared to be no induction of the proinsulin genetic construct over background in hepatocytes exposed to 3.3 or 5.5 mM glucose. The transfected hepatocytes express insulin mRNA only in response to glucose concentrations that fall within or above the physiological range. Strong induction is seen at glucose concentrations of greater than 5.5 mM.

Results of Northern analysis show that both glucose regulatory modules C and F confer glucose dependent inducibility to the same degree, although the AdFAM construct using the F module appears to be somewhat more responsive. Hepatocytes transfected with AdCMV-Ins, in which the proinsulin coding sequence is under control of the constitutive CMV promoter, generates RNA of the distinctive size without regard to glucose concentration.

Results of RNA quantitation by phosphoimaging are summarized in Table 1. There was only a slight difference in relative expression between 3.3 and 5.6 mM glucose, in contrast to a 3.06-fold increase in relative expression at glucose concentrations of 27.5 mM.

TABLE 1

Relative Transcription of Insulin mRNA in Hepatocytes

| Glucose (mM) | Hins mRNA | 18s RNA | Normalized hIns mRNA (hIns mRNA/18s RNA) | Hins mRNA (Relative* Expression) |
|---|---|---|---|---|
| 3.3 | 81074 | 56 | 787 | 0.91 |
| 5.6 | 51039 | 33 | 865 | 1.00 |
| 27.5 | 201056 | 40 | 2645 | 3.06 |

*For the sake of comparison, the normalized amount of insulin mRNA expressed at euglycemic level (5.6 mM glucose) is arbitrarily assumed to be one.

Example 6

Cloning of Insulin Construct with Rat Albumin 5' Untranslated Region and Truncated 3' Untranslated Region The proinsulin coding sequences of Example 3 were further modified by eliminating the 5' untranslated region of human insulin mRNA and replacing that region with the 5' untranslated region of rat albumin (bases 153-188 as published in GenBank Accession No. M16825, herein incorporated by reference; SEQ ID NO:24). This modification was accomplished by PCR amplification of hInsM2 using three oligonucleotide primers. Synthesis of one strand was performed using the oligonucleotide TA455 (SEQ ID NO:15) which comprises a KpnI recognition site, bases 153-188 of the albumin promoter corresponding to the 5'-untranslated region of albumin and a sequence corresponding to human proinsulin mRNA (starting with the first base of the codon specifying the first amino acid), TA452 (SEQ ID NO:16), which is complementary to the sequence that terminates at the end (base 392) of the insulin open reading frame, or TA454 (SEQ ID NO:17), which is complementary to the sequence that ends 18 bases after the termination codon of the insulin ORF. TA452 and TA454 each contain a Sal I restriction site to facilitate cloning of the products described in Example 1. The amplification product of TA455 and TA452 was designated M2A, and the amplification product of TA455 and TA454 was designated M2B.

Figure 5:
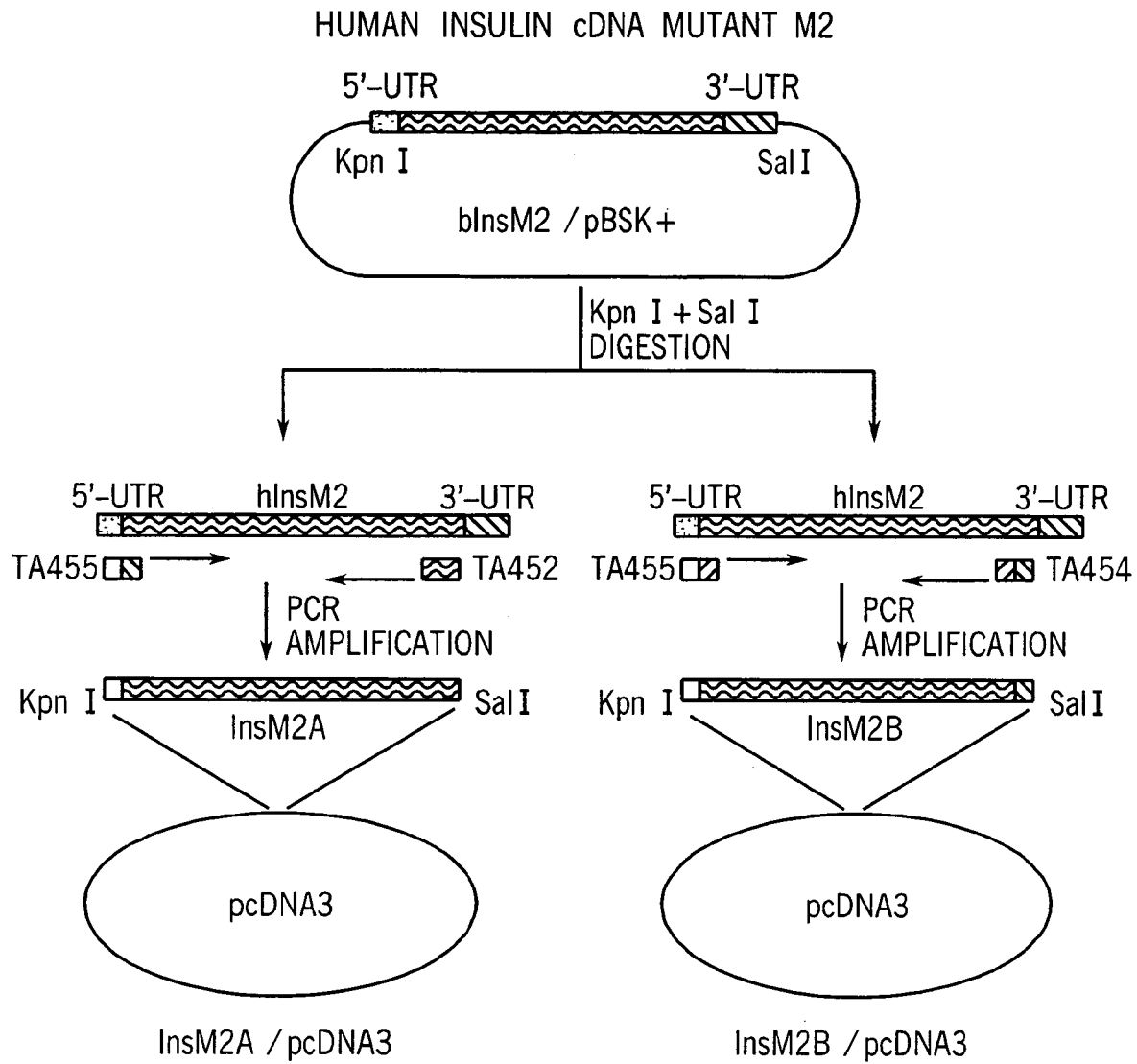
FIG. 5 is a schematic diagram of the steps used to clone M2A and M2B.

Following amplification, the chimeric sequences M2A and M2B were subcloned without their promoter sequences by digesting the amplified DNA with KpnI and by ligating to KpnI-EcoRV-digested plasmid vector pcDNA3 (Invitrogen, Madison, Wis.) which contains a CMV promoter, as shown schematically in FIG. 5. Following ligation, the plasmids were used to transform competent *E. coli* DH5α cells. Additional plasmid DNA was isolated from transformants, and plasmid DNA was introduced into Cos7 cells as described below.

Example 7

Secretion of Insulin from COS 7 Cells Transfected with Insulin Constructs Containing the 5'-Untranslated Region of Rat Albumin Cos7 cells were used to test the ability of the constructs described in Example 3 to synthesize and secrete insulin. The TRANS IT™ transfection reagent (PanVera Corp., Madison, Wis.) was used to transfect the Cos7 cells with plasmids containing the M2A and M2B mutants for transient expression. A four-hour period of incubation for transfection was followed by an overnight incubation of the cells in fresh DMEM supplemented with 10% fetal calf serum. The medium was then changed and the plates incubated for two days in medium containing either 10% or 5% fetal calf serum. The medium was collected and the cells were harvested separately. The cells were lysed in Tris-buffered saline (pH 7.6) containing 1% NP-40, a nonionic detergent, and protease inhibitors (trypsin inhibitor and PMSF). Both the medium and cell lysate were analyzed for the presence of insulin by antigen capture ELISA.

Figure 6:
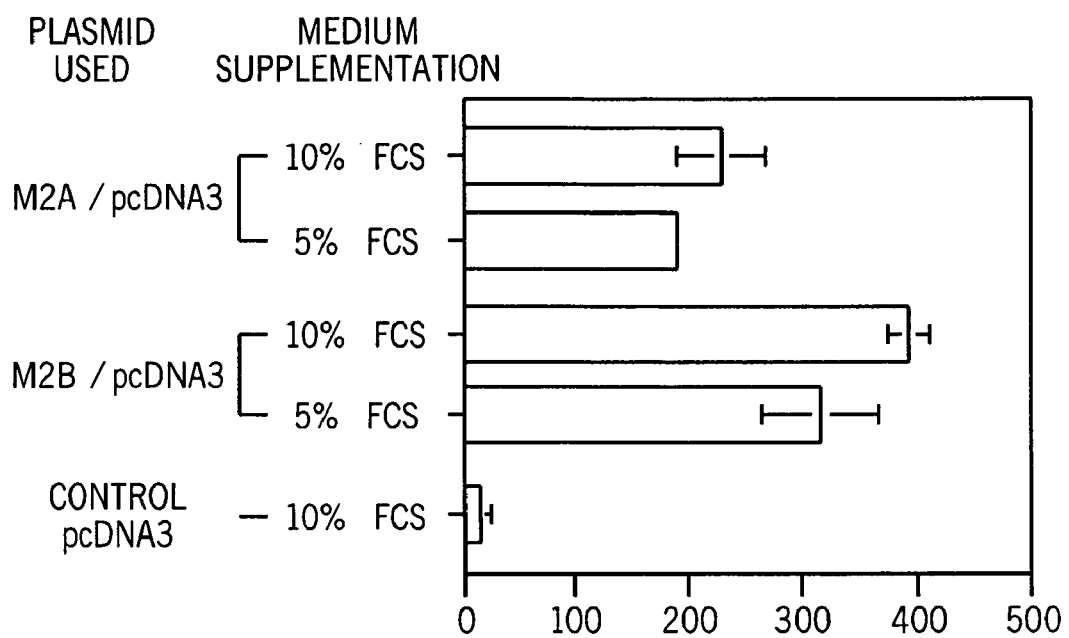
FIG. 6 is a graph showing total insulin released from lysed Cos7 cells transfected with recombinant plasmids.
Figure 7:
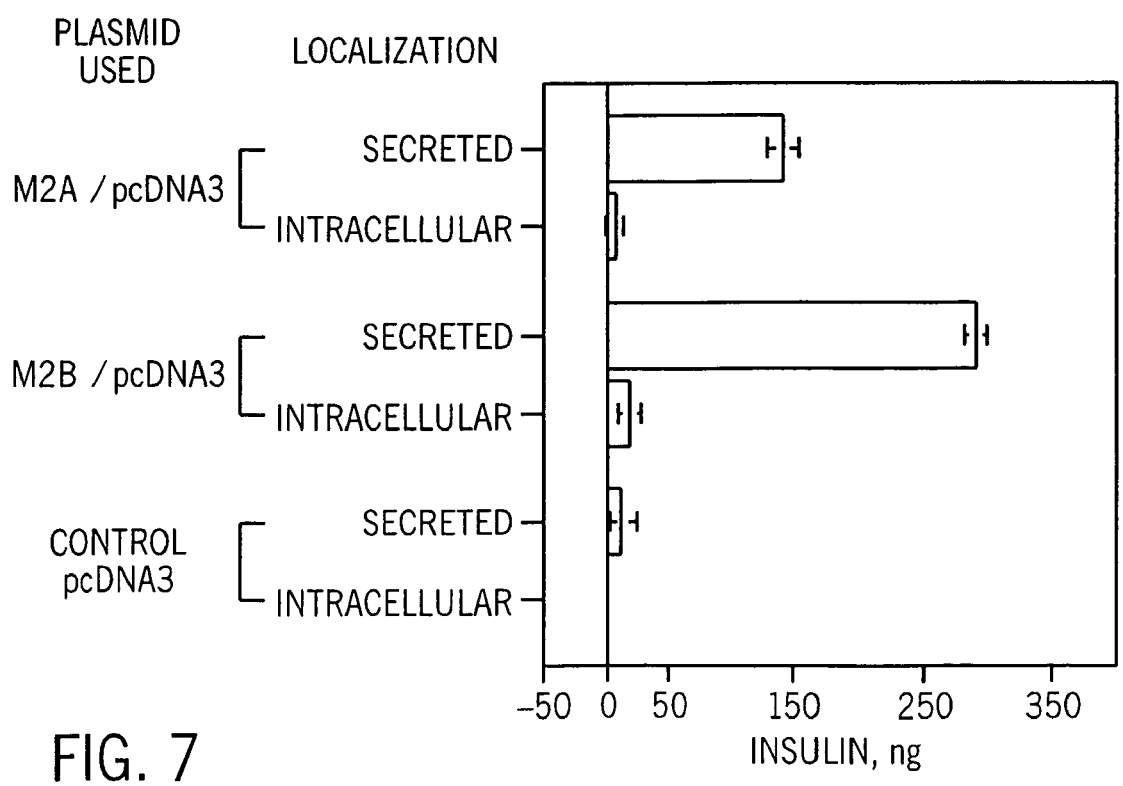
FIG. 7 is a graph showing intracellular and secreted insulin by Cos7 cells transfected with recombinant plasmids.

The results indicate that both M2A and M2B direct the synthesis of secretable insulin (FIGS. 6 and 7). Insulin production was higher in Cos7 cells transformed with the M2B construct. It is also apparent that the majority of the synthesized insulin is secreted (FIG. 7). Control cells transformed with the vector pcDNA 3 with no insert did not produce insulin.

Example 8

Construction of Chimeric Proinsulin Sequences Containing One or More Glucose Inducible Regulatory Element and Having the 5' UTR of Rat Albumin Three chimeric human insulin constructs in adenovirus, containing one, two or three GIRE units, an albumin promoter and a coding sequence for human proinsulin (including two mutations to aid furin-mediated processing of proinsulin to insulin) were prepared.

The general strategy of assembling the hIns constructs was essentially the same as described above. The sense and antisense oligonucleotides corresponding to one or two GIREs were chemically synthesized. The sequences of the sense oligonucleotides are shown in SEQ ID NO:8 and SEQ ID NO:9. Each set of oligonucleotide pairs was designed to have a recognition sequence for NotI and EcoRI at the 5'- and 3'-ends, respectively. An additional pair of oligonucleotides corresponding to one GIRE was made to contain EcoRI and XbaI sites on the 5' and 3' ends, respectively. The original sense oligonucleotide [TA420 (SEQ ID NO:6) or TA421 (SEQ ID NO:7)] was used for amplification of rat albumin promoter containing an EcoRI site and an XbaI site. A construct containing three GIREs (SEQ ID NO:10) was prepared using the oligonucleotides shown in SEQ ID NO:8 and SEQ ID NO:9 and standard molecular biological techniques.

The rat albumin promoter sequence bases 1-184 of the published sequence (Accession No. M61825, SEQ IS NO: 24) described earlier was extended by PCR to include the entire 5'-untranslated region of rat albumin. A sequence encoding the human proinsulin (M2B) containing point mutations in the sequences corresponding to the B-C and C-A junction of proinsulin obtained from constructs previously described was modified to eliminate the 5'-untranslated region arising from hIns cDNA by PCR. The two fragments of DNA were joined together by overlap extension in a PCR reaction. The product of this reaction contains (5'->3') albumin promoter, 5'-UTR of albumin and a coding sequence for human proinsulin comprising a modified C-A junction, i.e., a T->G mutation at base 257 of the open reading frame to yield an arginine residue at amino acid residue 62 of proinsulin in place of the leucine residue of native proinsulin (LQKR to RQKR) and a modified B-C junction of native proinsulin, i.e., KTRR to RTKR. This DNA fragment, which contains EcoRI and SalI recognition sequences at the 5' and 3'-ends, respectively, was digested with the two enzymes, mixed with the annealed pair of oligonucleotides corresponding to one or two GIREs, described above, and ligated to linearized pACdeltaCMV DNA.

Example 9

Glucose-Inducible Synthesis of Insulin in Hepatocytes

Figure 8A:
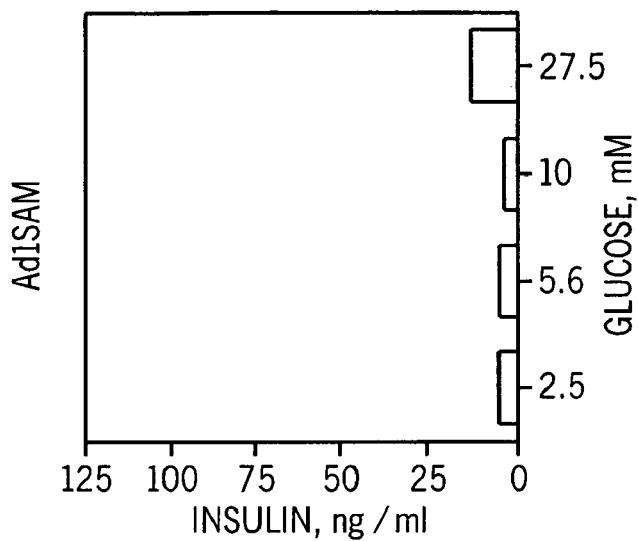
FIGS. 8A, 8B and 8C are graphs showing the production of insulin secreted into medium by hepatocytes transfected with a construct containing one, two or three GIREs, respectively, as a function of glucose concentration.
Figure 8B:
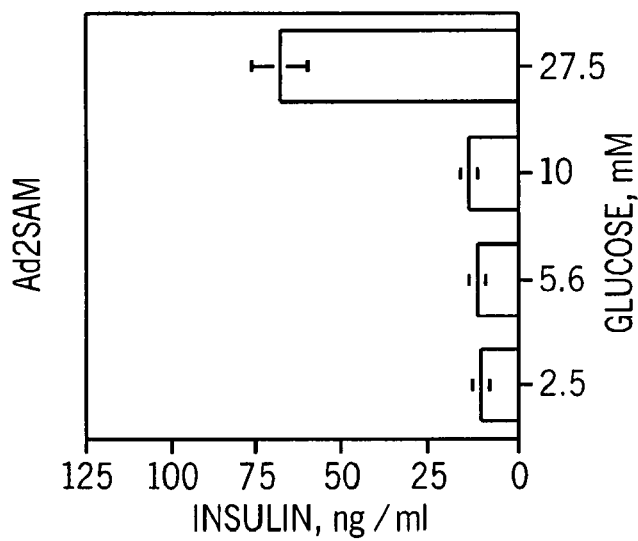
Figure 8C:
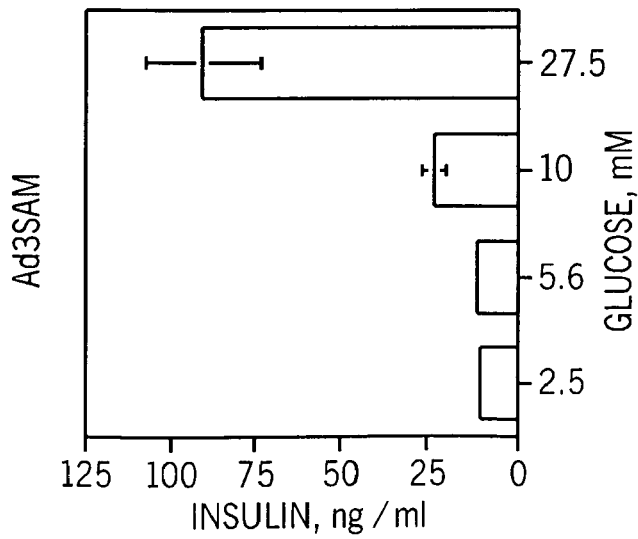

Vectors comprising insulin constructs comprising one, two or three GIREs were individually mixed with the plasmid pJM17 and the mixture of the two plasmid DNAs cotransfected into HEK 293 cells to generate recombinant replication-defective adenovirus (as described in Example 7, above). The sequence of each construct was confirmed by standard sequencing methods. Freshly prepared hepatocytes were plated on collagen-coated 30 mm plates and transfected with adenovirus containing insulin construct with one (Ad1SAM2B), two (Ad2SAM2B) or three (Ad3SAM2B) GIREs at a multiplicity of infection (MOI) of four. The sequences of each insert for Ad1SMA2B, Ad2SAM2B and Ad3SAMB are shown in SEQ ID NO:11, SEQ ID NO:12, and SEQ ID NO:13, respectively. The culture medium was changed 16 h post-transfection, with medium containing 2.5, 5.6, 10 or 27.5 mM glucose. The insulin secreted into the medium was assayed 32 hours after media change, by antigen capture ELISA (Table 4; FIG. 8A-C).

A glucose-dependent increase in the secreted insulin from transduced hepatocytes is clearly seen when the gene construct contains either two GIREs (FIG. 8B) or three GIREs (FIG. 8C). However, glucose dependent expression and secretion of insulin in cells transfected with Ad1SMA2B, which contains a single GIRE, was minimal (FIG. 8A). Furthermore, the construct containing three GIREs, in addition to a higher maximal induction at 27.5 mM glucose (approximately 9-fold increase over the level at 2.5 or 5.6 mM glucose as opposed to 6.5 fold increase in the case of construct with two GIREs under identical 25 conditions), also shows >2 fold increase in insulin secretion at 10 mM glucose.

TABLE 4

Amount of insulin secreted (ng/ml) by hepatocytes transfected with vectors containing one, two, or three GIREs in response to glucose challenge.

| Glucose, mM | Ad1SAM2B | Ad2SAM2B | Ad3SAM2B |
| --- | --- | --- | --- |
| 2.5 | 4.97 ± 1.09 | 9.09 ± 2.27 | 9.98 ± 1.37 |
| 5.6 | 5.12 ± 1.26 | 10.72 ± 2.30 | 10.80 ± 1.57 |
| 10.0 | 3.2 ± 1.8 | 13.2 ± 2.4 | 22.8 ± 4.1 |
| 27.5 | 12.75 ± 2.05 | 67.16 ± 10.24 | 90.33 ± 19.80 |

Example 10

Insulin Transcription of a GIBE Construct in Response to Physiological Levels of Glucose as a Function of Time Collagen coated 60 mm plates or dishes, each containing $1 \times 10^6$ hepatocytes, were transfected with Ad2SAM2B at a rate of $3.5 \times 10^6$ pfu/plate. Hepatocytes receiving no virus, or virus encoding bacterial β-galactosidase were included as controls. Hepatocytes were then exposed for 16 h to 5.6 mM glucose in RMPI supplemented with 10% fetal calf serum, 30 μg/mL proline, 5 μg/mL insulin, 5 μg/mL transferrin and 5 μg/mL selenium, at 37° C. The plates containing transfected cells were then divided into two groups; one group received fresh medium containing 5.6 mM glucose, the second group received fresh medium with 27.5 mM glucose. From each of these two groups, individual plates were removed after 30 min, 1 h, 2 h, 4 h, 8 h, and 16 h, the medium decanted, and the cells frozen in liquid nitrogen. Total RNA was extracted, separated electrophoretically and analyzed for hIns mRNA by northern blotting, as described above.

The results of northern blotting showed that hepatocytes transfected with Ad2SAM2B and exposed to 27.5 mM glucose contained detectable levels of hIns mRNA after 30 min, and that the hIns mRNA levels increased thereafter in a time-dependent manner. At the normal glucose level (5.6 mM), the signal was much lower. Quantitation of the bands revealed that hIns mRNA levels were approximately 10-fold higher in hepatocytes exposed to glucose concentrations of 27.5 mM than in hepatocytes exposed to glucose concentrations of 5.6 mM.

These data demonstrate that the vector construct containing two GIRES initiates transcription in response to elevated glucose levels in a time frame comparable to islet cells. Insulin mRNA production is increased in the presence of 5.6 mM glucose, the steady state concentration of glucose in the bloodstream, but is stimulated at relatively high concentrations of glucose (27.5 mM).

Example 11

Insulin Synthesis by Hepatocytes Transfected with Construct Containing Two GIREs Freshly prepared rat hepatocytes were transfected with two different adenovirus constructs containing the MI mutated proinsulin sequence: AdSAM1 (containing the rat albumin promoter modified to contain two GIREs) and AdCMVInsM1 (containing the constitutive and highly active CMV promoter). Hepatocytes transfected with AdCMV β-Gal and untransfected hepatocytes were used as controls. Four plates of hepatocytes were transfected with each adenovirus preparation; two plates were exposed to the low (3.3 mM) or high (27.5 mM) glucose concentrations. After 36 hours, hepatocytes were exposed for 16 hours to 5.6 mM or 27.5 mM glucose in RMPI supplemented with 2 mg/mL bovine serum albumin with leucine omitted, 30 µg/mL proline, 5 µg/mL insulin, 5 µg/mL transferrin and 5 µg/mL selenium, at 37° C.

Following a 6 h leucine depletion, a 2 mL aliquot of the low or high glucose containing defined medium was added to appropriate plates. For each tested recombinant adenovirus, one plate for each glucose concentration received 0.2 mCi $^3$H-leucine (500 Ci/mmole). The remaining plate received the equivalent amount of unlabelled leucine and at the end of all incubations it was used for viability determination.

The leucine incorporation was carried out for 16 h, followed by a 4 h chase with unlabeled leucine. The culture medium was aspirated, cell debris removed, and the supernatant analyzed for secreted insulin. The cells on each plate were lysed with 0.8 mL solution containing 20 mM Tris-HCL buffer at pH 7.6, 2 mM EDTA, 5 µg/mL trypsin inhibitor, 50 µM phenylmethane sulphonyl fluoride 30 (PMSF) and 1% Triton-X100. The lysate was centrifuged at 16,000×g for 10 min in a microcentrifuge, the pellet discarded, and the supernatant solution used for analysis of labeled intracellular products.

Each assay included 0.8 mL of culture supernatant or 0.4 mL of cell lysate supernatant. To minimize non-specific precipitation of labeled proteins, cultures were pre-treated with *Staphylococcus aureus* in the absence of specific antibodies. A 50 µL aliquot of a 10% suspension of formalin-fixed *Staphylococcus* cells (Calbiochem) was added to each tube; tubes were incubated at room temperature for 30 min with continuous mixing, centrifuged (4 min, 16,000×g), and the supernatant was used for further analysis. To immunoprecipitate insulin and insulin-related products, 2.5 µL of polyclonal guinea pig anti-human insulin (Sigma Chemical Co.) was added to the supernatant solution, mixed and kept at room temperature for 45 min, followed by addition of *Staphylococcus* cells, 30 min incubation and centrifugation as described above. The supernatant was discarded, and the pellet washed 4-5 times with 1 mL of 20 mM Tris-HCl at pH 7.6, 0.15 M NaCl and 0.1% Triton X-100. To control for sample to sample variation, a 2 µL aliquot of rabbit anti-rat albumin polyclonal antiserum was included along with anti-insulin antiserum to a series of duplicate samples treated as described above to co-precipitate human insulin and endogenous rat albumin.

Each pellet was suspended in a 40 µL aliquot of a solution containing 60 mM Tris-HCl at pH 6.8, 1.2% SDS, 2% β-mercaptoethanol, heated at 100° C. for 4 min, centrifuged, and the supernatant analyzed by polyacrylamide-SDS gel electrophoresis. Specificity of the immunoprecipitated material was established by the use of control cells transduced with β-galactosidase and untransfected cells. The identity of the immunoprecipitated material was confirmed in a separate set of test samples to which unlabeled insulin or rat serum was added to provide competition with labeled insulin or albumin respectively, and tubes processed simultaneously.

The optimum gel system for resolution of insulin B and A chains and rat albumin was found to be an SDS/Tris-Tricine 10-20% linear polyacrylamide gradient based on the description of Schagger and Jagow (Anal. Biochem. 166:368-379, 1987). A 15 µL aliquot of SDS-BME-treated immunoprecipitated material from each sample was resolved on the gel along with peptide size markers from BioRad. The gels were fixed, stained, destained, soaked in "Amplify" solution (Amersham), dried under vacuum, and exposed to X-ray film at −80° C.

The results showed the presence of an anti-insulin antibody-binding band in cell extracts of hepatocytes transduced with AdSAM1 (glucose inducible) and AdCMV.InsM1 (constitutive). AdSAM1 contains two glucose inducible regulatory elements coupled to the rat albumin promoter, and AdCMV.InsM1 contains the cytomegalovirus immediate/early promoter. When AdSAM1 was used, the insulin band appeared only in the hepatocytes exposed to high glucose (27.5 mM) and was not evident in cells exposed to low glucose (3.3 mM). In contrast, cells transfected with AdCMV.InsM1 and exposed to 3.3 mM or 27.5 mM glucose produced insulin in roughly equal amounts.

The size of the insulin positive band was determined to be 7,700 Daltons, which differs somewhat from the sizes of mature insulin B and A chains. The size of rat albumin was determined to be 67,000 Daltons, which compares favorably with the known size. Band signals were essentially eliminated in samples in which unlabelled insulin or albumin was added. Densitometry revealed that insulin expression in cells transfected with AdSAM1 and exposed to high glucose concentrations was only about 20-fold lower than in cells in which insulin expression is driven by the constitutive promoter CMV, one of the strongest known promoter in most in vivo and ex vivo mammalian systems.

These data demonstrate the synthesis of insulin in response to physiological levels of glucose in hepatocytes transfected with a vector containing the proinsulin coding sequence under the control of two GIREs. At 3.3 mM glucose, there is no detectable sythesis of insulin; at 27.5 mM glucose, insulin synthesis is readily detectable. By adding two GIREs to the vector, which provide an additional control mechanism at the transcriptional level, the synthesis of insulin is correctly regulated in the appropriate physiological range. Synthesis of insulin mRNA and insulin are increased at glucose concentrations exceeding 5.6 mM and are not synthesized or are synthesized at very low levels in cells exposed to glucose concentrations of 5.6 mM. This feature makes vectors containing GIREs suitable for treating Type I diabetes.

Example 12

Glucose Tolerance Testing of Normal, Treated, or Untreated Diabetic Rats

Figure 9:
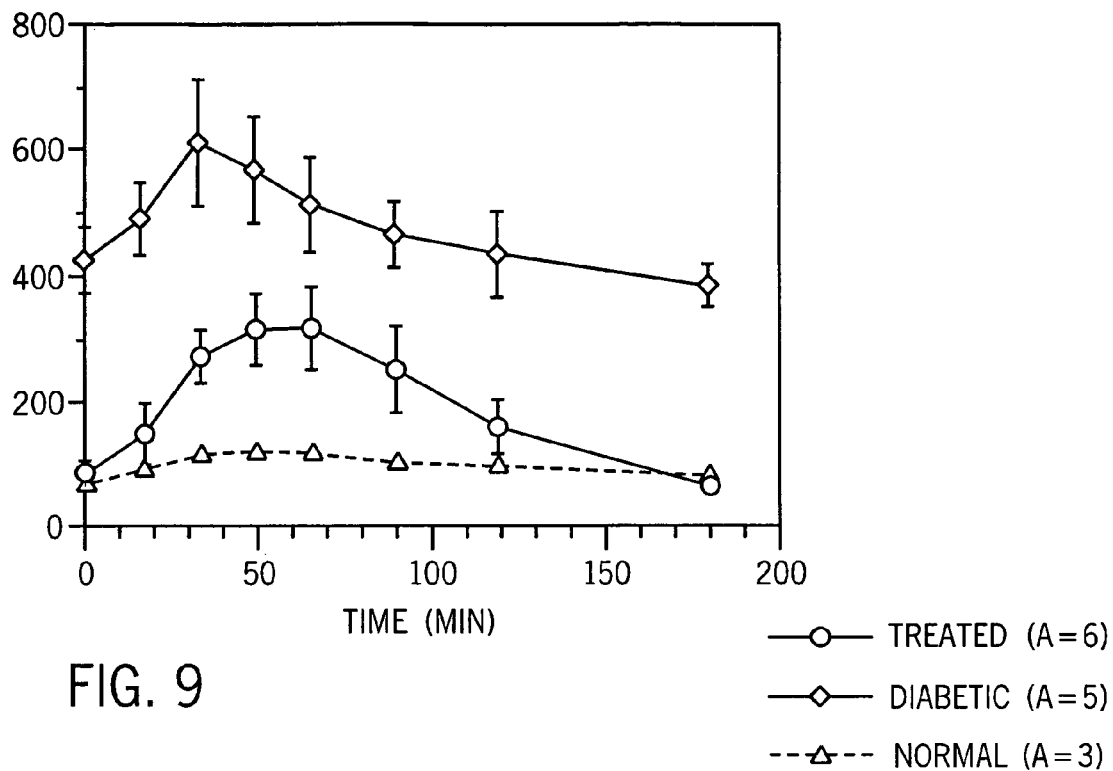
FIG. 9 shows blood glucose levels for normal, treated diabetic and untreated diabetic rats immediately prior to (time 0) and at various times after oral administration of glucose.

Lewis rats (Harlan) fed an ad lib diet of Purina rat chow were fasted overnight, treated with 80 mg/kg streptozotocin (SZ) intravenously (i.v.) to induce a diabetic state, and injected with $1 \times 10^{12}$ pfu/rat of Ad3SAM2B using phosphate buffered saline (10 mM Na phosphate, 0.15 m NaCl pH 7.5) as the vehicle. Injections were made at three to four different sites in the liver. Controls included untreated SZ-diabetic and normal rats. At ten days post infection, the animals were fasted overnight and fed glucose at a rate of 2 g glucose/kg body weight. Blood was collected from the rats just prior to and at various times after the glucose feeding to determine blood glucose levels. FIG. 9 shows the glucose levels as a function of time for treated SZ-diabetic, untreated SZ-diabetic, and normal rats.

The results demonstrate that blood glucose levels of treated SZ-diabetic and normal rats were comparable just prior to and two to three hours after oral glucose dosing. In contrast, glucose levels in untreated SZ-diabetic rats were about four fold higher than the treated and normal rats at these time point, and the peak glucose level was approximately two-fold higher than that of the treated SZ-diabetic rat. Similar results were obtained on the $7^{th}$ day after gene therapy.

Example 13

Figure 10:
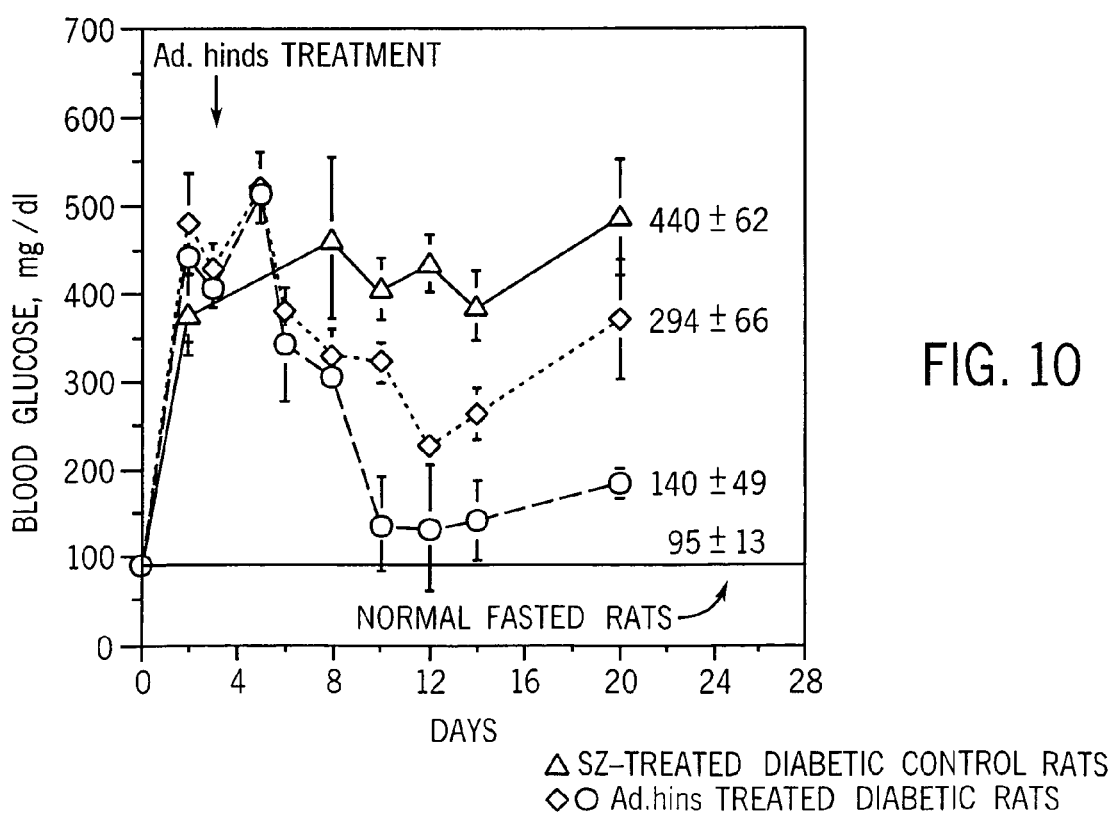
FIG. 10 shows fasting blood glucose levels for normal, treated diabetic and untreated diabetic rats.

Kinetics of Blood Glucose Reduction in Normal, Untreated or Treated Diabetic Rats Lewis rats (Harlan) were fasted overnight and treated intravenously (i.v.) with 80 mg/kg SZ. Three days after the SZ treatment, rats were injected at three to four different sites in the liver with Ad3SAM2B at a rate of either $1 \times 10^{12}$ pfu or $2 \times 10^{12}$ pfu using phosphate buffered saline (10 mM Na phosphate, 0.15M NaCl, pH 7.4). Fasting blood glucose levels for normal and for untreated or for treated SZ-diabetic rats were measured following overnight fasts for 20 days, and the results are shown in FIG. 10. The grey line and the shaded area represent the fasting blood glucose levels of normal control rats (mean±SD). The 10-day average blood glucose (mean±SD) of each group is shown to the right of each curve.

The results demonstrate that insulin gene therapy in accordance with the present invention significantly reduced fasting blood glucose levels of diabetic rats. The reduction in blood glucose levels was viral dose-dependent.

In summary, the present invention provides a method for glucose-regulated production of active insulin in non-islet cells in which insulin is not naturally produced by providing the cells with a genetic construct containing a nucleotide sequence encoding proinsulin operably connected to a promoter functional in the cell under the control of one or more glucose inducible regulatory elements. Glucose regulation by insulin so produced is maintained in the physiological range.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

Example 14

Translational Enhancement Improves Glucose-Dependent Hepatic Insulin Expression and Reduces Hyperglycemia in STZ-Induced Diabetic Rats Gene-therapy based hepatic insulin production is a promising strategy in the treatment of insulin dependent diabetes mellitus (IDDM). We have previously shown (see Examples above) that hepatocytes engineered with Ad.3SAM2 to produce transgenic insulin improved glucose tolerance tests and corrected fasting hyperglycemia in streptozotocin (STZ)-induced diabetic rats. However, due to insulin insufficiency, postprandial hyperglycemia was not fully corrected. In this study, to increase the insulin output we generated a new insulin gene construct (Ad.SATEM) containing a translational enhancer sequence derived from mouse vascular endothelial growth factor (VEGF) from plasmid pcDNA4/His-MaxA (Invitrogen) corresponding to 917 bp-1079 bp. Primary rat hepatocytes ($1 \times 10^6$ cells) transduced with Ad.SATEM showed a 3.6-fold increase in human insulin secretion (430.3 ng/ml) compared to Ad.3SAM2 (120.3 ng/ml) over a period of 24 hours in 27.5 mM glucose, while glucose responsiveness was still maintained. In vivo studies using STZ-induced diabetic rats demonstrated that treatment with Ad.SATEM compared to Ad.3SAM2 significantly increased insulin serum concentration under both postprandial (14.9±1.9 µU/ml and 6.2±0.8 µU/ml, respectively) and fasting (5.9±1.2 µU/ml and 2.9±1.1 µU/ml, respectively) conditions (P<0.001), thus accelerating kinetics to restore postprandial euglycemia. Both Ad.3SAM2 and Ad.SATEM treated groups showed a significant reduction of postprandial hyperglycemia and reduced weight-loss compared to diabetic control animals. In conclusion, we have demonstrated that enhancing the translational efficacy in our preproinsulin construct SATEM substantially improves the insulin secretion in vitro and in vivo.

Figure 12:
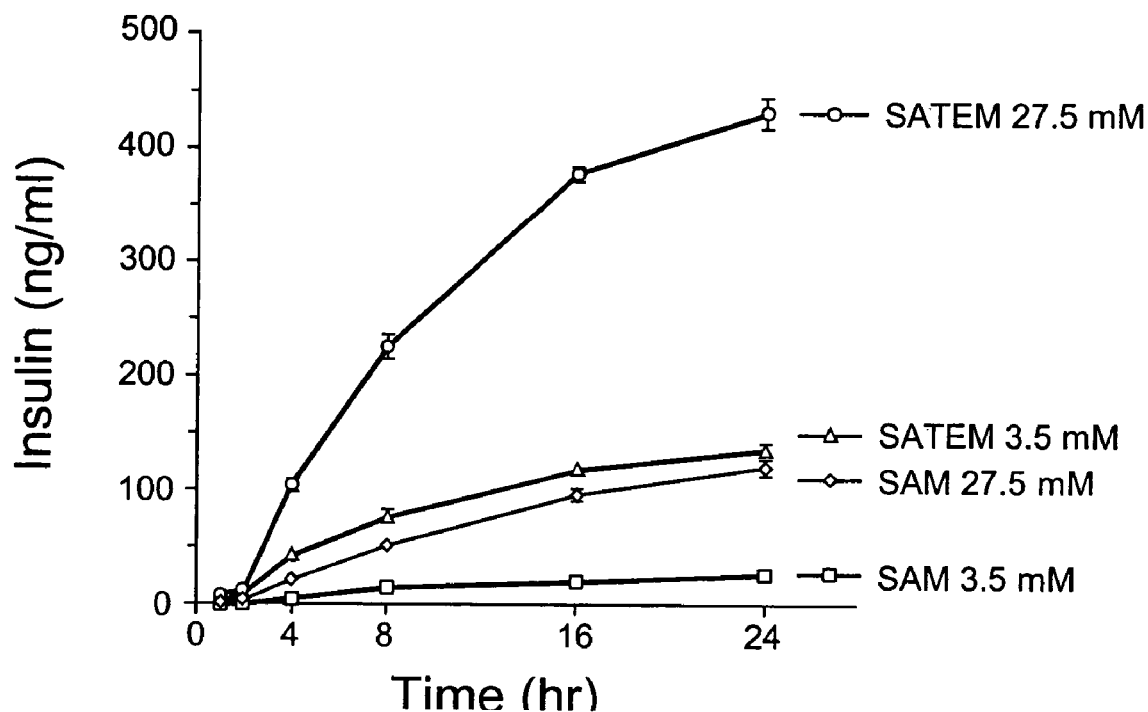
FIG. 12 illustrates the effect of Ad.3SAM2 and Ad.3SATEM on total amount of expressed insulin from transfected primary rat hepatocytes over a period of 24 hours.

Transduction of Primary Hepatocytes with Ad.3SAM2 and Ad.3SATEM and Kinetics of Insulin Secretion Kinetic studies for glucose dose-response were performed using both Ad.3SAM2 and Ad.SATEM to determine if the translational enhancer sequence incorporated into Ad.SATEM affects the kinetic and magnitude of insulin secretion. Primary rat hepatocytes were transfected side-by-side with Ad.3SAM2 or Ad.SATEM and medium supplemented with either 3.5 mM or 27.5 mM glucose. After one hour, a detectable increase in insulin (1.33 ng/ml) was measured in the medium of cells treated with Ad.SATEM at a glucose concentration of 27.5 mM but none was detected in medium from Ad.3SAM2 treated cells. The correlation between glucose concentration in the medium and insulin secretion was dose-dependent for both Ad.3SAM2 and Ad.3SATEM, the glucose-dependent insulin secretion was significantly higher in magnitude for Ad.SATEM compared to Ad.3SAM2, both at low and high glucose concentrations (FIG. 12). Thus, primary hepatocytes exposed to Ad.SATEM showed a glucose-stimulated insulin expression that ranged from 136±9 ng/ml at 3.5 mM to 430±23 ng/ml at 27.5 mM glucose after 24 hours compared to Ad.3SAM2 where the amount was was 26±5 ng/ml to 120±12 ng/ml at 3.5 mM and 27.5 mM glucose, respectively (FIG. 12).

Treatment of STZ-Induced Diabetic Rats with Ad.3SAM2 and Ad.SATEM

Figure 13A:
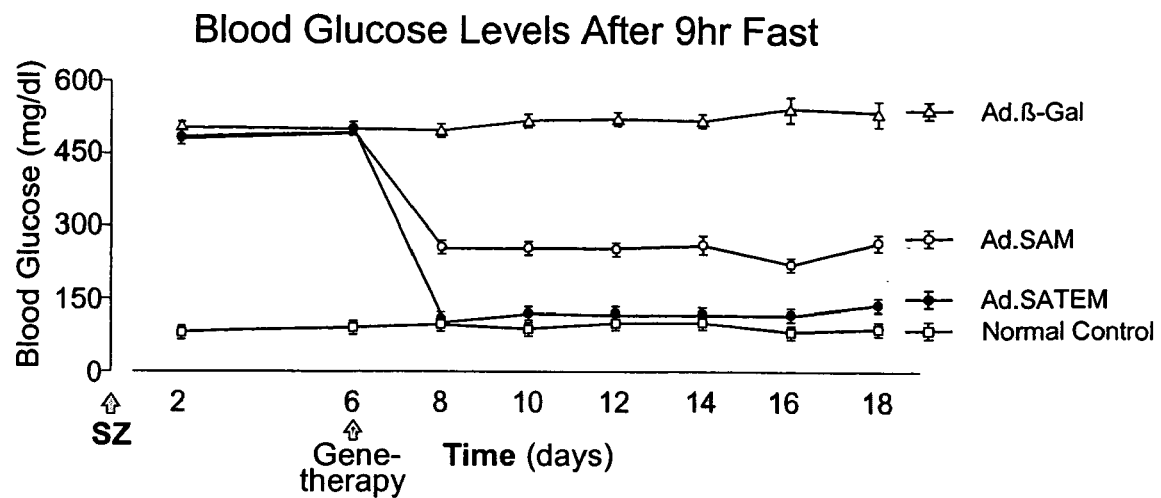
FIGS. 13A and 13B illustrate the effect of in situ insulin gene therapy on blood glucose levels (A) and body weight (B) of diabetic rats.
Figure 13B:
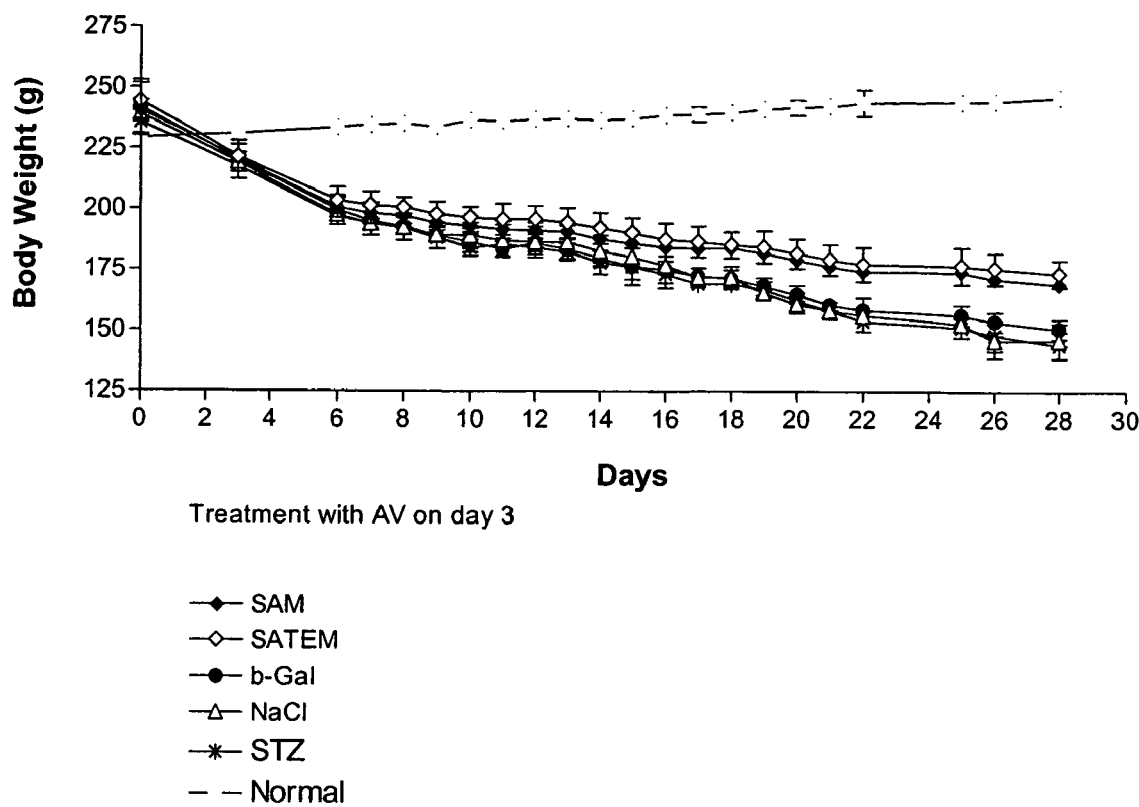

To evaluate the effect of translational enhancement of hepatic insulin expression on postprandial blood glucose levels in vivo, STZ-induced diabetic rats (75 mg/kg) were tested with an equal vector dose (0.4 ml of $2.2 \times 10^{11}$ infectious units/ml) of either Ad.3SAM2 (n=6), Ad.SATEM (n=6) or Ad.CMV.β-Gal (n=3); additional controls were either injected with the same volume of 0.15M NaCl carrier alone (n=3) or remained untreated (n=3). While nondiabetic animals (n=3) maintained normal blood glucose levels (97±13 mg/dl) and gained weight continually over time, the control-treated diabetic animals treated with Ad.CMV.β-Gal or sham-treated with 0.15M NaCl suffered from chronic hyperglycemia (605±51 mg/dl) and severe weight loss as did the untreated diabetic animals (n=3) (FIG. 13B). Ad.SATEM treated animals still showed moderate hyperglycemia under fed ad libitum conditions, but fasting blood glucose levels were significantly lower (84±26 mg/dl) than in Ad.3SAM2-treated animals (241±81 mg/dl; P<0.05), as shown in FIG. 13A. Weight loss was decreased during the period of the experimental observation (FIG. 13B), which is in agreement with our previous observations demonstrating that sustained transgenic insulin expression by Ad.3SAM2 in STZ-induced diabetic rats significantly reduces progressive weight loss compared to diabetic control animals (Alam, T., Sollinger H: 2002, *Transplantation* 74:1781-1787).

Figure 14A:
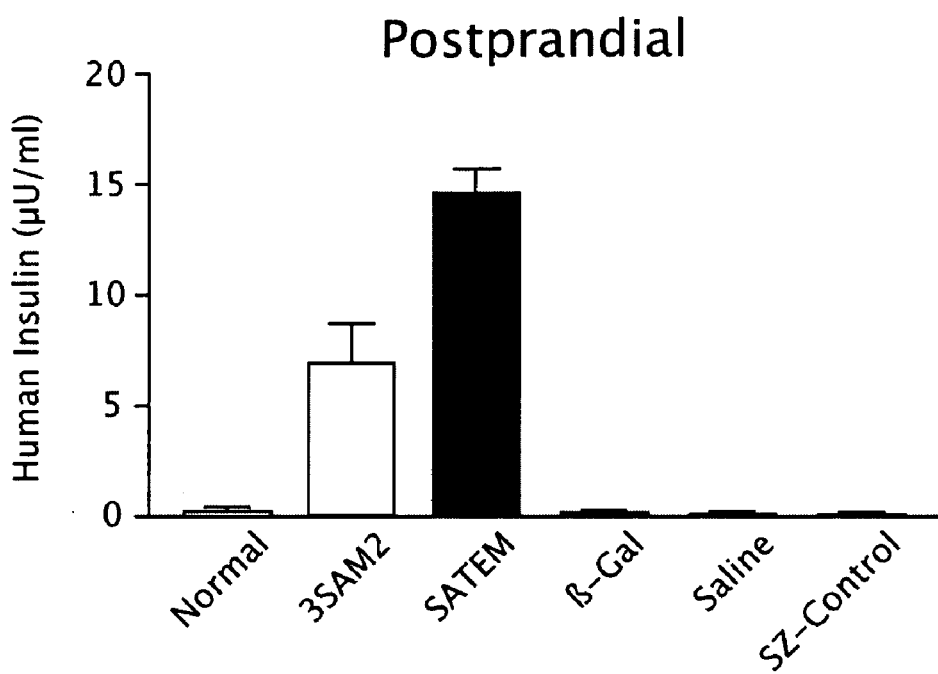
FIGS. 14A and 14B illustrate serum levels of human insulin (A) and rat C-peptide (B) in diabetic rats subjected to insulin gene therapy.
Figure 14A:
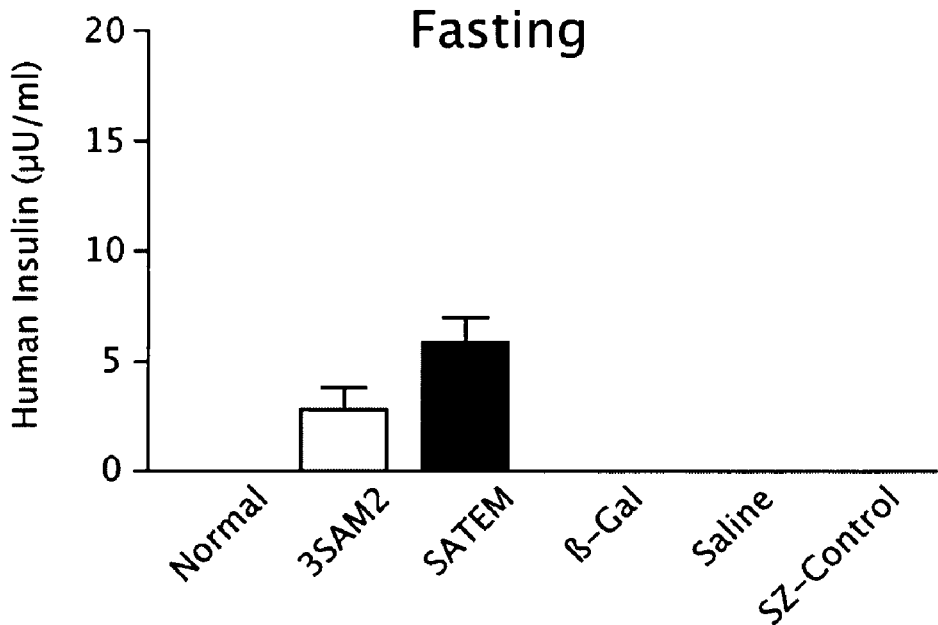
Figure 14B:
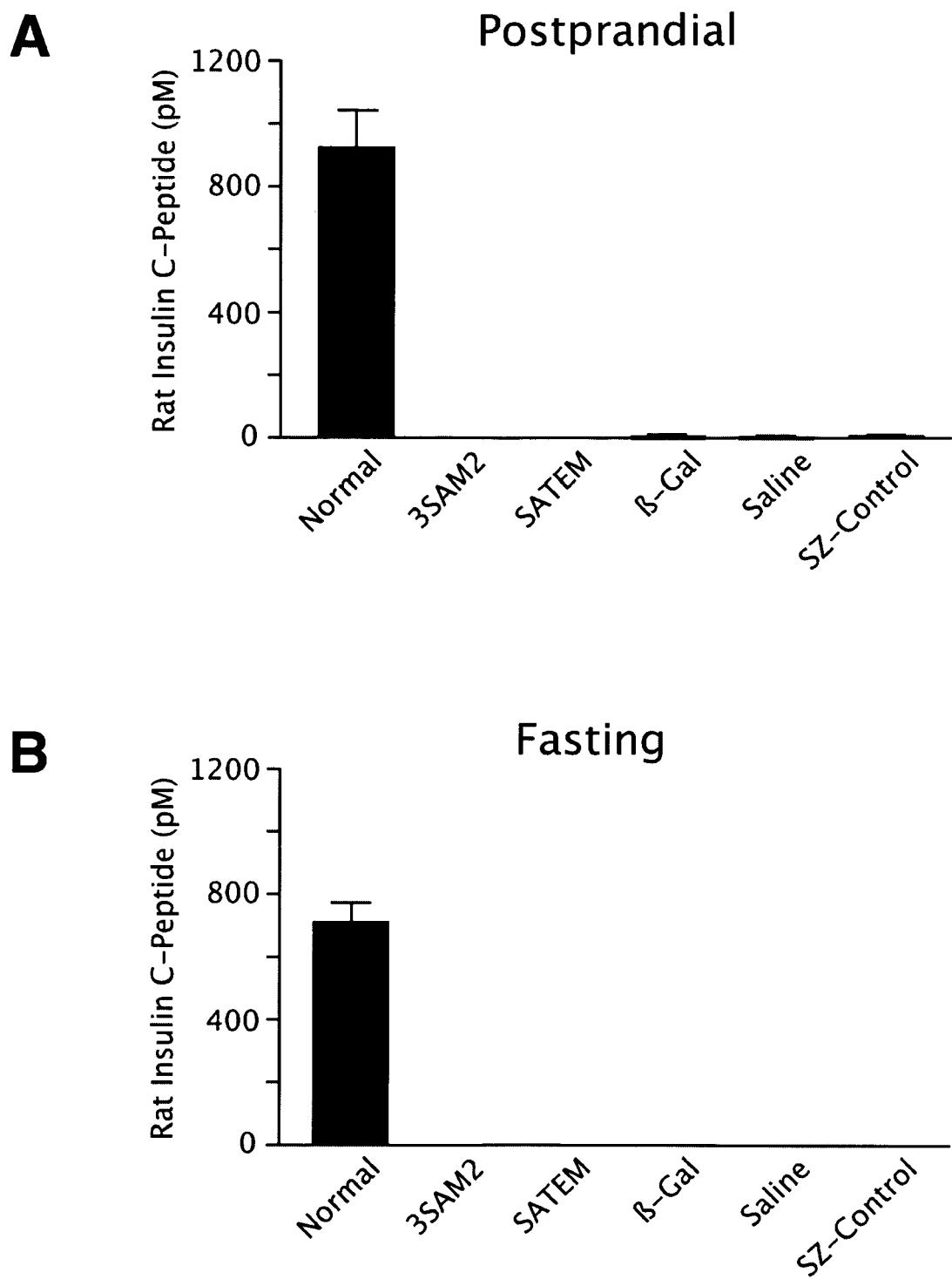

Human insulin levels in serum of Ad.3SAM2- and Ad.SATEM-treated animals, fed ad lib, were 6.2±0.8 and 14.9±1.9 µU/ml, respectively, after 5 days of gene delivery whereas human insulin was not detectable in the serum of all other control-treated or untreated animals (FIG. 14). While rat C-peptide levels in the serum of non-diabetic control animals remained normal, 169±36 µM and 874±133 µM, in fasting and fed, ad libitum, all other animals that underwent STZ-treatment showed C-peptide levels at or below the lowest level of reliable detection, indicating an essentially complete β-cell destruction (FIG. 14).

To determine how well insulin secretion by translationally enhanced Ad.SATEM corrects postprandial blood glucose levels and therefore is capable to accelerate kinetics to restore euglycemia compared to Ad.3SAM2, all animals from the above experiment were fasted overnight. Blood samples were collected to assess blood glucose, plasma human insulin, and rat C-peptide levels prior to fasting and at various time intervals after fasting, namely after 3 hours, 6 hours and 9 hours. Nondiabetic control animals maintained blood glucose levels in a narrow range between 65 mg/dl and 110 mg/dl. Blood glucose levels of diabetic rats fed ad libitum, starting at 487±50 mg/dl and 422±50 mg/dl in Ad.3SAM2- and Ad.SATEM-treated diabetic animals, respectively, declined to 438±49 and 270±45 mg/dl after 3 hours, 321±56 and 150±44 mg/dl after 6 hours, and 241±81 and 84±26 mg/dl after 9 hours of fasting, while blood glucose levels of Ad.C-MV.ββ-Gal-, 0.15M NaCl-treated and non-treated diabetic control animals continued to remain elevated at 507±30 mg/dl. Although differences in blood glucose levels between Ad.3SAM2 and Ad.SATEM were statistically not significant under fed ad libitum conditions (P>0.05), blood glucose levels in Ad.3SATEM-treated animals decreased significantly faster than in Ad.3SAM2-treated animals (P<0.05). In Ad.3SATEM-treated animals complete correction of postprandial hyperglycemia was achieved after a fasting period of nine hours compared to thirteen hours in Ad.3SAM2-treated animals. At the end of the fasting period concentrations of human insulin in the serum of Ad.3SAM2- and Ad.3SATEM-treated animals were significantly reduced to 2.9±1.1 µU/ml and 5.9±1.2 µM, respectively. Also, rat C-peptide measured in nondiabetic control animals declined from 874±133 µM before to 169±36 µM after fasting, whereas the C-peptide levels in all other diabetic animals remained low (FIG. 14).

Figure 15:
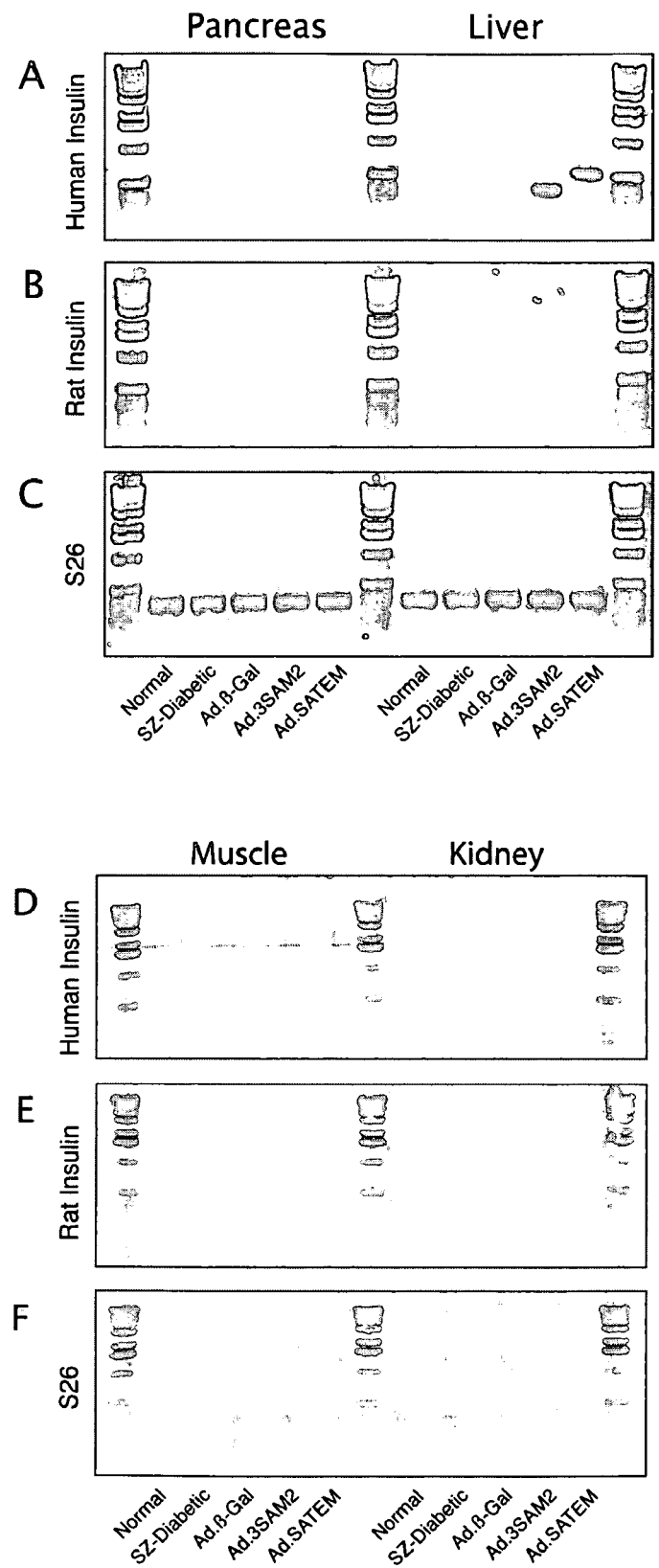
FIG. 15 illustrates the detection of human insulin mRNA in livers, pancreas, muscle and kidneys of different experimental rat groups.
Figure 16:
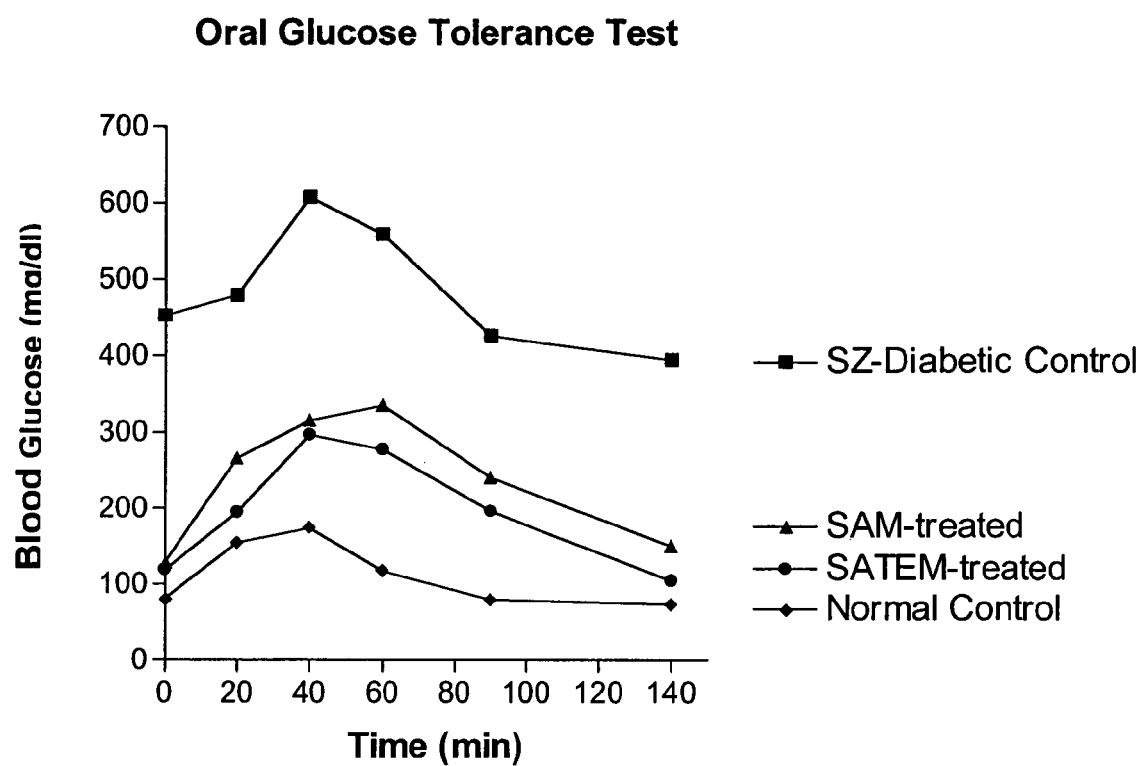
FIG. 16 illustrates OGT and food challenge.

An indirect analysis of in vivo kinetics of insulin release and function was performed by oral glucose tolerance tests (2 gm glucose/kg body weight) on all animals fasting for nine hours except for the Ad.3SAM2-treated group which was fasted for thirteen hours to obtain fully corrected blood glucose levels (110±12 mg/dl) as observed in the Ad.SATEM-treated group after nine hours. The results showed that fasting blood glucose levels (time 0 min) of non-diabetic, Ad.3SAM2-, and Ad.SATEM-treated diabetic rats were comparable (FIG. 15). Approximately 140 min after oral glucose ingestion blood glucose measured in Ad.SATEM-treated animals returned to initial levels (108 mg/dl). Compared to Ad.CMV.β-Gal-, 0.15M NaCl-treated, and non-treated diabetic control rats, Ad3SAM2- and Ad.SATEM-treated animals showed a marked reduction in peak glucose levels, but were not different among each other (P>0.05). Therefore the oral glucose tolerance test (2 g glucose/kg body weight) was modified: instead of oral glucose ingestion, after fasting animals were given access to a limited amount of food. Each experimental rat was kept in an individual cage and provided with standard rodent chow (4% of body weight), which was constantly available to animals during the food challenge experiments. Blood glucose levels were then measured at 30 minutes intervals for 2.5 hours. Unlike the oral glucose tolerance test, blood glucose levels remained significantly lower during this food challenge in the Ad.SATEM-treated group compared to Ad3SAM2-treated animals (P<0.05), indicating that elevation in blood glucose caused by modest portions of food ingestion may be corrected by SATEM gene construct with greater ease than 3SAM2.

Pancreas, liver, muscle, and kidney specimens from Ad.3SAM2-, Ad.3SATEM-, Ad.CMV.β-Gal-, NaCl-treated, and non-treated STZ-diabetic as well as from nondiabetic rats were used to extract RNA. Detection of mRNA for human insulin, rat insulin I and II, and ribosomal protein S26 was performed by RT-PCR (FIG. 15). The observed comparable signal for an invariant ribosomal protein S26 indicated that an approximately equal amount of cellular material was used from each tissue sample in PCR. The results of PCR amplification indicated the presence of human insulin mRNA in the liver tissue of Ad.3SAM2- and Ad.3SATEM-treated diabetic rats, as the rat insulin I and II transcripts were present in the pancreas of normal rats but absent in the pancreas of STZ-treated diabetic rats, regardless of Ad3SAM2- or Ad.3SATEM-treatment, demonstrating that STZ completely destroyed the β-cells of normal rats. Since oligonucleotides used for detection of rat insulin I and II mRNA contain an extensive similarity to human insulin sequence, using rat insulin I and II primers, a weak signal was observed in the livers of Ad3SAM2- and Ad.3SATEM-treated diabetic rats. Human or rat insulin mRNA was not present in the muscle or kidney tissue of any of the animals from the five groups, as expected (FIG. 15).

Discussion

Our previously described insulin construct 3SAM2 (Alam T., Sollinger H: 2002, *Transplantation* 74:1781-1787) has been shown to cause a glucose dependent insulin secretion from liver to correct fasting hyperglycemia in STZ-diabetic rats. However, 3SAM2 was unable to fully correct postprandial hyperglycemia. In order to improve the capacity of 3SAM2 to produce larger amount of insulin to overcome insulin insufficiency during postprandial period, the strategy described herein is designed to increase the efficiency of insulin translation. Because hepatic insulin production lacks the use of β-cell like regulated secretory pathways and depends only on transcriptional regulation, any alteration in preproinsulin mRNA to prolong its life could increase overall insulin output but it entails increasing an undesirable alternation risk for prolonged exposure to hypoglycemia caused by continued production of insulin in the post-euglycemic phase in vivo. By incorporation of a translational enhancer sequence derived from VEGF into our previously described 3SAM2 insulin construct (Alam T, Sollinger H: 2002, *Transplantation* 74:1781-1787) we created a modified construct (3SATEM), which contains three S14-based GIREs, the liver-specific albumin promoter, and furin cleavage compatible human insulin cDNA whose activity for transcription is stimulated by glucose (FIG. 11). Because the chimeric promoter/enhancer construct was new, we verified the efficacy in side-by-side experiments with 3SAM2. The results of transient transfection experiments confirm that the GIREs, the albumin promoter, and the translational enhancer, each remain functional. To evaluate optimal MOI for the in vitro experiments we exposed primary rat hepatocytes at a high glucose concentration (27.5 mM) to an increasing dose but equal amount of infectious units of both Ad.3SAM2 and Ad.3SATEM (FIG. 12) and compared the amount of secreted insulin. The increase of insulin secretion due to translational enhancement through Ad.3SATEM was high, demonstrating that improving the efficiency of mRNA translation increases the quantity of secreted human insulin from hepatocytes in response to glucose exposure. Differences in measured insulin output at low and high glucose concentrations in the supernatant from transduced hepatocytes remained proportional over time: 3 to 4-fold throughout the duration of 24 hours indicating that insulin output retains glucose responsiveness and this increased amount of insulin might help overcome postprandial hyperglycemia in vivo. Glucose concentrations used for the in vitro experiments resided within a typical range of fasted normal (~60 mg/dl glucose; 3.5 mM) and a STZ-induced diabetic rats (~500 mg/dl glucose; 27.5 mM). In both, short-term (between one and 4 hours) and long-term studies (between 8 and 24 hours), primary hepatocytes' glucose responsiveness under low and high glucose conditions showed a distinct glucose-mediated upregulation.

In the past, an inability to coordinate transgenic insulin secretion with rapidly changing demands for insulin action has limited the efficiency of insulin gene-therapy models in vivo. We recently reported that Ad.3SAM2 transferred to livers of chemically induced diabetic rats showed significant reduction of postprandial hyperglycemia compared with diabetic control animals and complete correction of fasting glucose. Using the Ad.3SATEM, a better correction of hyperglycemia was expected as confirmed by our results. The difficulty of reconstructing the highly regulated insulin secretion of β-cells is the major obstacle in near ideal glucose-regulation by insulin expression in hepatocytes since hepatic insulin expression is based on the constitutive secretory pathway, but our results provide further support to the idea that liver cells with the ability to secrete insulin, regulated by glucose-dependent transcription, may serve as an adequate alternative for treatment of IDDM in the future.

Material and Methods

Adenoviral Vector Construction

Generating 3SATEM from 3SAM2 (Alam T. Sollinger H: 2002, *Transplantation* 74:1781-1787) (FIG. 11)

DNA fragment (Not I/Sal I) from p. 3SATEM was inserted in the adenovirus shuttle plasmid p.ACCMV.pLpA(Becker) after removing the existing CMV promoter contained in the 0.6 kb NotI-SalI DNA-fragment. These shuttle vectors were used to clone SATEM in an E1-deleted replication-defective adenovirus vector. Ad.3SATEM as described previously {Becker, T. C., Noel, R. J., Coats, W. S., et al., *J. Biol. Chem.* 1994; 43:161; Gomez-Foix, A. M., Coats, W. S., et al. *J. Biol. Chem.* 1992; 267: 25129; Alam, T., Sollinger, H.: 2002, *Transplantation* 74:1781-1787) with one modification: co-transfection of adenovirus plasmids into HEK 293 cells (ATCC, Manassas, Va.) was mediated by DOTAP (Roche Molecular Biochemicals, Indianapolis, Ind.). Synthetic capacity of the transgene was verified by insulin enzyme-linked immunosorbent assay (ELISA) (Eckhoff. D. E., Sollinger H. W., Hullett, D. A., *Transplantation* 1991; 51:1161) of medium conditioned by primary cultured hepatocytes infected with crude lysates of expanded viral plaques. Ad.3SAM2 and Ad.3SATEM were prepared by CsCl (Sigma) equilibrium density gradient centrifugation and stored before use at −80° C. Adenoviral titers were determined by Adeno-X Rapid Titer Kit (Clontech, Palo Alto, Calif.) as per the manufacturer's instructions.

Cell Culture and Transduction

Primary hepatocytes were isolated from male Lewis rats (150-250 g, Harlan Sprague Dawley, Indianapolis, Ind.) by in situ perfusion of collagenase A (Mannheim Boehringer Biochemicals, Indianapolis, Ind.), as described previously (>90% viability by eosin) (Gomez-Foix, A. M., Coats, W. S., et al., *J. Biol. Chem.* 1992). $1 \times 10^6$ cells were plated on collagen-coated six-well culture plates (Falcon/Becton Dickinson Labware, Lincoln Park, N.J., USA) in DMEM culture medium (Cellgro Mediatech Inc., Herndon, Va.) containing 10% fetal calf serum (Hyclone, Logan, Utah), 5 µg/ml transferin (ICN Biochemicals Inc., Aurora, Ohio), 5 µg/ml selenium (Collaborative Biochemical Products, Bedford, Mass.), and 5.6 mM glucose (Sigma-Aldrich Corporation, St. Luis, Mo.). After attachment of hepatocytes to the culture dishes (three) hours, the medium was replaced with fresh medium containing 5.6 mM glucose and adenovirus containing human insulin constructs Ad.3SAM2 or Ad.3SATEM, as indicated. The controls included Ad.CMV.β-Gal treated or non-transfected hepatocytes. The culture medium was replaced four hours after transfection with fresh medium containing concentrations of glucose between 3.5 mM and 27.5 mM. Secreted insulin in the collected culture medium was measured by enzyme-linked immunosorbent assay (ELISA) (Eckhoff, D. E., Sollinger, H. W., Hullett, D. A., *Transplantation* 1991; 51:1161). Each test was performed in triplicate, and all of these experiments have been repeated at least three times.

Animal Experiments

All animal studies were performed on male Lewis rats, (150-250 g, Harlan Sprague Dawley), housed in pairs in individual cages, and exposed to 12-hour-cycles of light and dark (06:00 am-06:00 pm). All procedures were approved by the University of Wisconsin Animal Care and Use Committee and followed the guidelines of the National Research Council. Unless otherwise specified, animals were provided water and standard rodent chow (Purina) ad libitum.

Diabetes in the rats was induced by intravenous administration of streptozotocin (STZ) (Sigma Aldrich Corporation), at a dose of 75 mg/kg through the penile vein. The STZ treatment rendered all rats diabetic within 24 hours (blood glucose≧400 mg/dl). They where then divided into experimental groups, as indicated. Blood glucose levels were measured with glucose reagent strips and glucometer (Bayer Diagnostic, Mishawaka, Ind.) using a small drop of blood obtained from a tail vein.

One week following STZ-injection animals underwent surgery for direct liver injections of Ad.3SAM2 and Ad.3SATEM, or control treatment with either Ad.CMV.β-Gal or carrier alone (0.9% NaCl) or remained untreated. Surgical anesthesia was achieved by inhalation of isoflurane (Abbott Laboratories, North Chicago, Ill.). A 2 to 3 cm midline incision was made to gain access to their livers. Ad.3SAM2-treated diabetic animals received a vector dose of $1.2 \times 10^{11}$ infectious units/ml as did Ad.3SATEM- and Ad.CMV.β-Gal-treated diabetic animals, while NaCl-treated diabetic animals received injections of an equivalent volume. The infectious dose was determined by Adeno-X Rapid Titer System (Clontech), Periodic fasting and fed ad libitum serum blood glucose levels of all the rats were measured. Fasting periods usually started between 05:00 and 06:00 pm. Serum for human insulin and rat C-peptide RIA (Linco Research, St. Charles, Mo.) was obtained via jugular venipuncture and was and stored in aliquots at −20° C. prior to evaluation. Tissue samples of pancreas, liver, kidney and muscle used for detection of insulin mRNA from various groups of experimental rats were excised three weeks after adenovirus treatment, frozen in liquid nitrogen, and stored at −80° C. until used for RNA extraction.

Glucose Tolerance Test

Glucose tolerance was assessed by oral administration of 40% glucose solution (Sigma-Aldrich Corporation) at a dose of 2 g/kg body weight. Blood samples were collected from a small cut at the tip of tail for glucose determination before fasting, before glucose injection, and at 30 minutes intervals during the first 2.5 hours.

Human Insulin and Rat C-Peptide RIA

Concentrations of human insulin in rat serum were determined using human insulin specific RIA which were known to have 0.1% or less cross-reactivity with rat insulin, and less than 0.2% cross-reactivity with human proinsulin (Linco Research). Rat C-peptide was measured using RIA with less than 0.1% cross-reactivity to human C-peptide, human insulin, or human proinsulin (Linco Research).

RT-PCR

Human insulin mRNA was detected by RT-PCR using 3SAM2 and 3SATEM construct-specific primers. The forward primer 5'-GTCMCCCACTGCCTCTGG-3' (SEQ ID NO:26) corresponds to the rat albumin 5'-UTR-derived region and the backward primer 5'-TGCAGGCT-GCGTCTAGTTG-3' (SEQ ID NO:27) corresponds mostly to the 3'-UTR of the human insulin sequence. The primers selected for PCR amplification of the rat insulin genes (both 1 and 11) were from conserved regions of sequences (forward primer, 5'-CTGCCCAGGCTTTTGTCAAA-3' (SEQ ID NO:28); backward primer, 5'-TATTCATTGCA-GAGGGGTGG-3' (SEQ ID NO:29)). The amplification of S26 (Vincent, S. et al., *Nucleic Acids Res*. 21: 1498, 1993), an invariant ribosomal protein used as a marker of the amount of mRNA, was performed by using 5'-TCGTGC-CAAAAAGGGCCG-3' (SEQ ID NO:30) as forward and 5'-GCTCCTTACATGGGCTTTGGTGG-3' (SEQ ID NO:31) as backward primers.

Statistics

Means and standard errors of the mean were calculated using either GraphPad Prism 3 (GraphPad Software Inc., San Diego, Calif.), or Excel 2002 (Microsoft Corporation, Redmond, Wash.). Data are reported as mean±standard deviation (SD). P-value was considered significant if ≦0.05 and calculated using the one-tailed t-test, assuming unequal variances.

We claim:

1. A genetic construct for glucose-regulated synthesis of active insulin in a host cell in which insulin is not natively produced, comprising
    a promoter functional in the host cell;
    a coding sequence for a human proinsulin, the coding sequence operably connected to the promoter, wherein the human proinsulin encoded by the coding sequence comprises amino acid sequences corresponding to B-C and C-A junctions of native human proinsulin that are cleavable in the host cell;
    a glucose responsive regulatory module located 5' of the promoter, the module having at least one glucose inducible regulatory element comprising a pair of CACGTG motifs linked by a five base nucleotide sequence; and
    an untranslated region not natively associated with the coding sequence for human proinsulin, wherein the untranslated region is located 5' of the coding sequence and 3' of the promoter.

2. The genetic construct of claim 1, wherein the 5' untranslated region is characterized by reduced formation of secondary structures by intramolecular base pairing, relative to the formation of secondary structures by the 5' untranslated region natively associated with the coding sequence for human insulin.

3. The genetic construct of claim 1, wherein the regulatory module comprises at least two glucose inducible regulatory elements.

4. The genetic construct of claim 1, wherein the proinsulin encoded by the coding sequence comprises a modified C-A junction and a modified B-C junction, the modified C-A junction corresponding to a conversion of the amino acid sequence LQKR to RQKR and the modified B-C junction corresponding to the conversion of the amino acid sequence KTRR to RTKR.

5. An isolated host cell comprising the genetic construct of claim 1.

6. The genetic construct of claim 1, wherein the module comprises a sequence selected from the group consisting of SEQ ID NO:9 and SEQ ID NO:10.

7. An isolated virus infective for a host cell, the isolated virus comprising
    a promoter functional in the host cell;
    a coding sequence for a human proinsulin, the coding sequence operably connected to the promoter, wherein the human proinsulin encoded by the coding sequence comprises amino acid sequences corresponding to the B-C and C-A junctions of native human proinsulin that are cleavable in the host;
    a glucose responsive regulatory module located 5' of said promoter, the module having at least one glucose inducible regulatory element comprising a pair of CACGTG motifs linked by a five base nucleotide sequence; and a 5' untranslated region not natively associated with the coding sequence for human proinsulin, wherein the 5' untranslated region is located 5' of the coding sequence and 3' of the promoter.

8. The virus of claim 7, wherein the host cell is a hepatocyte.

9. The construct of claim 1, wherein the construct additionally comprises a translational enhancer sequence, wherein the translational enhancer sequence is operably connected to the promoter.

10. The construct of claim 9, wherein the translational enhancer sequence is obtained from the group consisting of the vascular endothelial growth factor gene translational enhancer sequence and internal ribosomal entry sites (IRES) from BiP, EFG, PDGF-B, IGF-II, and eIF4G.

11. The construct of claim 10, wherein the translational enhancer comprises residues 310-472 of SEQ ID NO:25.

12. The construct of claim 9 wherein the translational enhancer sequence is upstream of the coding sequence.

13. The construct of claim 9 wherein the translational enhancer sequence is downstream from the promoter.

* * * * *

UNITED STATES PATENT AND TRADEMARK OFFICE
CERTIFICATE OF CORRECTION

| | | |
|---|---|---|
| PATENT NO. | : 7,425,443 B2 | Page 1 of 1 |
| APPLICATION NO. | : 11/127629 | |
| DATED | : September 16, 2008 | |
| INVENTOR(S) | : Tausif Alam et al. | |

It is certified that error appears in the above-identified patent and that said Letters Patent is hereby corrected as shown below:

In the Specification

Column 14, line 38 "hins" should be --hlns--
Column 14, line 42 "hins" should be --hlns--

Signed and Sealed this
Second Day of September, 2014

Michelle K. Lee
*Deputy Director of the United States Patent and Trademark Office*